(12) United States Patent
Potter et al.

(10) Patent No.: US 12,172,631 B2
(45) Date of Patent: Dec. 24, 2024

(54) CONTROLLING AN AGRICULTURAL VEHICLE BASED ON SOIL DAMAGE SCORE/FILL LEVEL

(71) Applicant: Deere & Company, Moline, IL (US)

(72) Inventors: Benjamin C. Potter, Hudson, IA (US); Eric A. Keen, Manhattan, KS (US); Mark D. Klein, Ankeny, IA (US); Lee A. Johnson, Polk City, IA (US)

(73) Assignee: Deere & Company, Moline, IL (US)

( * ) Notice: Subject to any disclaimer, the term of this patent is extended or adjusted under 35 U.S.C. 154(b) by 271 days.

(21) Appl. No.: 17/715,407

(22) Filed: Apr. 7, 2022

(65) Prior Publication Data

US 2023/0234559 A1    Jul. 27, 2023

Related U.S. Application Data

(63) Continuation-in-part of application No. 17/581,272, filed on Jan. 21, 2022, and a continuation-in-part of application No. 17/581,297, filed on Jan. 21, 2022.

(51) Int. Cl.
*B60W 30/02*     (2012.01)
*A01B 69/04*     (2006.01)
(Continued)

(52) U.S. Cl.
CPC .......... *B60W 30/02* (2013.01); *A01B 69/008* (2013.01); *A01B 79/005* (2013.01);
(Continued)

(58) Field of Classification Search
CPC ... B60C 23/002; B60C 23/08; B60C 23/0479; A01B 79/005; G01C 21/20
See application file for complete search history.

(56) References Cited

U.S. PATENT DOCUMENTS 6,029,106 A    2/2000  Hale
6,041,582 A    3/2000  Tiede et al.
(Continued)

FOREIGN PATENT DOCUMENTS

DE    102009025494 A1 *  1/2011  ........... B60C 23/066
EP    1493599 A2          1/2005
(Continued)

OTHER PUBLICATIONS

Extended European Search Report and Written Opinion issued in European Patent Application No. 23163772.9, dated Aug. 17, 2023, in 07 pages.
(Continued)

*Primary Examiner* — George C Jin

(74) *Attorney, Agent, or Firm* — Kelly, Holt & Christenson; Joseph R. Kelly

(57) ABSTRACT

A soil measure, such as a soil cone index, and a vehicle index indicating the amount of force the vehicle exerts on the ground as it travels over the ground, are obtained and compared to identify a soil damage score. The soil damage score can be mapped over a field and an agricultural vehicle can be controlled based upon the soil damage score. In another example, a detector detects a fill level of a material storage compartment on an agricultural vehicle. The inflation pressure of tires on the agricultural vehicle is controlled based upon the detected fill level.

18 Claims, 21 Drawing Sheets

(51) Int. Cl.
| | |
|---|---|
| A01B 79/00 | (2006.01) |
| B60C 23/04 | (2006.01) |
| B60K 35/00 | (2024.01) |
| B60W 30/188 | (2012.01) |
| G01C 21/00 | (2006.01) |
| G01N 33/24 | (2006.01) |
| G05D 1/00 | (2006.01) |
| B60K 35/22 | (2024.01) |
| B60K 35/28 | (2024.01) |

(52) U.S. Cl.
CPC .......... B60C 23/0486 (2013.01); B60K 35/00 (2013.01); B60W 30/188 (2013.01); G01C 21/3826 (2020.08); G01N 33/24 (2013.01); G05D 1/0214 (2013.01); B60C 2200/08 (2013.01); B60K 35/22 (2024.01); B60K 35/28 (2024.01); B60K 2360/166 (2024.01); B60W 2300/15 (2013.01); G01N 33/245 (2024.05)

(56) References Cited

U.S. PATENT DOCUMENTS

| | | | |
|---|---|---|---|
| 10,315,655 B2* | 6/2019 | Blank | B60W 10/30 |
| 10,675,924 B2* | 6/2020 | Milburn, Jr. | B60C 23/0401 |
| 10,918,008 B2 | 2/2021 | Shearer | |
| 2007/0068238 A1* | 3/2007 | Wendte | B60C 23/002 |
| | | | 73/146 |
| 2012/0323452 A1 | 12/2012 | Green et al. | |
| 2013/0046418 A1* | 2/2013 | Anderson | E02F 9/2054 |
| | | | 701/1 |
| 2017/0066325 A1 | 3/2017 | Brownell | |
| 2020/0254829 A1* | 8/2020 | Schott | B60C 23/0479 |
| 2021/0008934 A1* | 1/2021 | Buhrke | B60C 23/002 |
| 2021/0276222 A1 | 9/2021 | Datema | |

FOREIGN PATENT DOCUMENTS

| | | |
|---|---|---|
| EP | 3216628 A1 | 9/2017 |
| EP | 2508057 B1 | 7/2018 |
| EP | 3415345 A1 | 12/2018 |
| EP | 2744322 B1 | 11/2019 |
| EP | 3763551 A1 | 1/2021 |
| WO | WO 03/023396 A2 | 3/2003 |
| WO | WO 2013/025890 A1 | 2/2013 |
| WO | WO 2013/112929 A2 | 8/2013 |

OTHER PUBLICATIONS

Extended European Search Report and Written Opinion issued in European Patent Application No. 23152289.7, dated Jun. 21, 2023, in 7 pages.
Extended European Search Report and Written Opinion issued in European Patent Application No. 23152290.5, dated Jun. 22, 2023, in 8 pages.
U.S. Appl. No. 17/581,272 Office Action dated Dec. 18, 2023, 8 pages.
U.S. Appl. No. 17/581,297 Application and Drawings filed on Jan. 21, 2022, 47 pages.
U.S. Appl. No. 17/581,272 Application and Drawings filed on Jan. 21, 2022, 47 pages.

* cited by examiner

CONTROLLING AN AGRICULTURAL VEHICLE BASED ON SOIL DAMAGE SCORE/FILL LEVEL

CROSS-REFERENCE TO RELATED APPLICATION

The present application is a continuation-in-part of and claims priority of U.S. patent application Ser. No. 17/581,297, filed Jan. 21, 2022, and U.S. patent application Ser. No. 17/581,272, filed Jan. 21, 2022, the content of which are hereby incorporated by reference in their entirety.

FIELD OF THE DESCRIPTION

The present description relates to agricultural machines. More specifically, the present description relates to agricultural vehicles that have a load that varies as the agricultural vehicle travels across a field.

The present description also relates to mobile work machines. More specifically, the present description relates to detecting a fill level of material on an agricultural vehicle and controlling tire inflation based upon the fill level.

BACKGROUND

There are a wide variety of different types of agricultural vehicles. Some such vehicles include sprayers, seeders and planters, air seeders, harvesters, nutrient spreaders, baling equipment, etc. All of these types of agricultural vehicles operate in a field and vary in weight over the course of the field.

The loads in these vehicles vary because the amount of material that is being gathered from the field (e.g., harvested), or applied to the field (e.g., sprayed), changes as the vehicle travels over the field. This can affect a number of things. For example, as the vehicle travels over the soil, it can inflict damage on the soil, such as undesired levels of compaction, among other things. Similarly, heavier vehicles may be more likely to become stuck in muddy areas or other areas within the field.

Some of these types of machines have a tire inflation system which can vary the inflation pressure in the tires of the vehicle. Other machines have a traction control system which can vary the torque applied to the ground engaging elements (e.g., wheels, tracks, etc.) different axels of the machine in order to increase traction.

In addition, the soil cone index is a measure of the strength of the soil, or a measure of the ability of the soil to carry a load. A cone penetrometer is a device which measures the force that it takes to push an element of the cone penetrometer tool into the soil. Thus, the cone penetrometer tool provides a soil cone index which indicates the ability of the soil to bear a load, and can also be an index indicative of the level of compaction of the soil.

The discussion above is merely provided for general background information and is not intended to be used as an aid in determining the scope of the claimed subject matter.

SUMMARY

A soil measure, such as a soil cone index, and a vehicle index indicating the amount of force the vehicle exerts on the ground as it travels over the ground, are obtained and compared to identify a soil damage score. The soil damage score can be mapped over a field and an agricultural vehicle can be controlled based upon the soil damage score. In another example, a detector detects a fill level of a material storage compartment on an agricultural vehicle. The inflation pressure of tires on the agricultural vehicle is controlled based upon the detected fill level.

Example 1 is a computer implemented method, comprising:
  obtaining a soil measure for soil indicative of an ability of the soil to bear a load;
  obtaining a vehicle index indicative of a force imparted by an agricultural vehicle on the soil, as a load corresponding to the agricultural vehicle varies as the agricultural vehicle travels over the field;
  comparing the soil measure to the vehicle index to obtain a comparison result;
  identifying a soil damage value based on the comparison result; and
  generating a control signal to control the agricultural vehicle based on the soil damage value.

Example 2 is the computer implemented method of any or all previous examples wherein obtaining a soil measure comprises:
  obtaining a plurality of different soil measure values, each soil measure value corresponding to a different geographic location across a field.

Example 3 is the computer implemented method of any or all previous examples wherein obtaining a vehicle index comprises:
  identifying a plurality of different vehicle index values, each vehicle index value corresponding to a different geographic location across the field.

Example 4 is the computer implemented method of any or all previous examples wherein comparing the soil measure to the vehicle index comprises:
  comparing each different soil measure value corresponding to a geographic location to a different vehicle index value corresponding to the geographic location.

Example 5 is the computer implemented method of any or all previous examples wherein identifying a plurality of vehicle index values comprises:
  identifying the plurality of different vehicle index values accounting for the variation in the load as the agricultural vehicle travels along a travel path.

Example 6 is the computer implemented method of any or all previous examples wherein identifying the plurality of different vehicle index comprises:
  identifying a set of vehicle characteristics corresponding to the agricultural vehicle; and
  identifying the plurality of different vehicle index values accounting for the variation in the load as the agricultural vehicle travels along a travel path and based on the vehicle characteristics of the agricultural vehicle.

Example 7 is the computer implemented method of any or all previous examples wherein obtaining a plurality of different soil measure values comprises:
  obtaining a map of each of the soil measure values mapped to the different corresponding geographic location.

Example 8 is the computer implemented method of any or all previous examples wherein obtaining a plurality of different soil measure values comprises:
  obtaining, as the plurality of different soil measure values, a plurality of different cone index scores.

Example 9 is the computer implemented method of any or all previous examples wherein the agricultural vehicle is a planting machine and wherein obtaining a plurality of different soil measure values comprises:

detecting down force and down force margin on the planting machine; and obtaining, as the plurality of proxy soil measure values, a plurality of proxy soil measure values based on the detected down force and down force margin.

Example 10 is the computer implemented method of any or all previous examples wherein obtaining a plurality of different soil measure values comprises:

obtaining a set of field characteristics corresponding to the field; and predicting the plurality of different soil measure values based on the set of field characteristics.

Example 11 is the computer implemented method of any or all previous examples wherein obtaining a set of field characteristics comprises:

obtaining terrain data indicative of terrain along a travel path traveled by the agricultural vehicle across the field;

obtaining soil type data indicative of a soil type of the soil along the travel path; and obtaining soil moisture data indicative of soil moisture along the travel path.

Example 12 is an agricultural system, comprising:

at least one processor; and a data store that stores computer executable instructions which, when executed by the at least one processor cause the at least one processor to perform steps comprising:

obtaining a soil measure for soil indicative of an ability of the soil to bear a load;

obtaining a vehicle index indicative of a force imparted by an agricultural vehicle on the soil, as a load corresponding to the agricultural vehicle varies as the agricultural vehicle travels over the field;

comparing the soil measure to the vehicle index to obtain a comparison result;

identifying a soil damage value based on the comparison result; and generating a control signal to control the agricultural vehicle based on the soil damage value.

Example 13 is the agricultural system of any or all previous examples wherein obtaining a soil measure comprises:

obtaining a plurality of different soil measure values, each soil measure value corresponding to a different geographic location across a field.

Example 14 is the agricultural system of any or all previous examples wherein obtaining a vehicle index comprises:

identifying a plurality of different vehicle index values, each vehicle index value corresponding to a different geographic location across the field.

Example 15 is the agricultural system of any or all previous examples wherein comparing the soil measure to the vehicle index comprises:

comparing each different soil measure value corresponding to a geographic location to a different vehicle index value corresponding to the geographic location.

Example 16 is the agricultural system of any or all previous examples wherein identifying a plurality of vehicle index values comprises:

identifying the plurality of different vehicle index values accounting for the variation in the load as the agricultural vehicle travels along a travel path.

Example 17 is the agricultural system of any or all previous examples wherein obtaining a plurality of different soil measure values comprises:

obtaining a map of each of the soil measure values mapped to the different corresponding geographic location.

Example 18 is the agricultural system of any or all previous examples wherein obtaining a plurality of different soil measure values comprises:

obtaining a set of field characteristics corresponding to the field; and predicting the plurality of different soil measure values based on the set of field characteristics.

Example 19 is a computer system, comprising:

at least one processor; and a data store that stores computer executable instructions which, when executed by the at least one processor, cause the at least one processor to perform steps, comprising:

detecting a vehicle index based on a fill level of material in a material holding compartment on the agricultural vehicle;

identifying a target inflation pressure for the tires based on a load bearing characteristic of soil over which the agricultural vehicle is traveling and based on the vehicle index; and controlling a controllable tire inflation subsystem to adjust inflation pressure in the tires to the target inflation pressure.

Example 20 is the computing system of any or all previous examples wherein the soil measure identification system is configured to obtain a plurality of different soil measure values, each soil measure value corresponding to a different geographic location across a field, wherein the vehicle index identification system is configured to identify a plurality of different vehicle index values, each vehicle index value corresponding to a different geographic location across the field, and wherein the soil damage score generation system is configured to compare each different soil measure value corresponding to a geographic location to a different vehicle index value corresponding to the geographic location.

Example 21 is a computer implemented method of controlling an agricultural vehicle, comprising:

detecting a fill level of material in a material holding compartment on the agricultural vehicle; and automatically controlling a tire inflation pressure for tires on the agricultural vehicle based on the detected fill level.

Example 22 is the computer implemented method of any or all previous examples wherein automatically controlling a tire inflation pressure comprises:

identifying a target inflation pressure for the tires based on the fill level.

Example 23 is the computer implemented method of any or all previous examples wherein automatically controlling a tire inflation pressure comprises:

controlling a controllable tire inflation subsystem to adjust inflation pressure in the tires to the target inflation pressure.

Example 24 is the computer implemented method of any or all previous examples wherein controlling the controllable tire inflation subsystem comprises:

detecting a current inflation pressure in the tires; and controlling the controllable tire inflation subsystem based on the current inflation pressure and the target inflation pressure.

Example 25 is the computer implemented method of any or all previous examples wherein identifying a target inflation pressure comprises:

identifying a load on the tires based on the fill level; and identifying the target inflation pressure for the tires based on the load on the tires.

Example 26 is the computer implemented method of any or all previous examples wherein identifying the load comprises:
identifying a type of material in the material holding compartment; and
identifying the load based on the fill level and the type of material.

Example 27 is the computer implemented method of any or all previous examples wherein identifying a target inflation pressure comprises:
identifying a separate target inflation pressure corresponding to each of a plurality of different subsets of the tires and wherein automatically controlling the tire inflation pressure comprises controlling the controllable tire inflation subsystem to adjust each of the different subsets of the tires based on the corresponding target inflation pressure.

Example 28 is the computer implemented method of any or all previous examples wherein automatically controlling comprises:
detecting a tire inflation control trigger; and
automatically controlling the tire inflation pressure based on detecting the tire inflation control trigger.

Example 29 is the computer implemented method of any or all previous examples wherein detecting a tire inflation control trigger comprises:
detecting a geographic location of the agricultural vehicle; and
detecting the tire inflation control trigger based on the detected geographic location.

Example 30 is the computer implemented method of any or all previous examples wherein detecting the geographic location comprises:
detecting a distance traveled by the agricultural vehicle and wherein detecting the tire inflation control trigger comprises detecting the tire inflation control trigger based on the distance traveled.

Example 31 is the computer implemented method of any or all previous examples wherein detecting a tire inflation control trigger comprises:
detecting a change in the load on the tires; and
detecting the tire inflation control trigger based on the change in the load on the tires.

Example 32 is the computer implemented method of any or all previous examples wherein detecting a tire inflation control trigger comprises:
detecting a change in the fill level of the material in the material holding compartment; and
detecting the tire inflation control trigger based on the change in the fill level.

Example 33 is an agricultural system, comprising:
an agricultural vehicle having a material holding compartment and a set of tires;
a level sensor detecting a fill level of material in the material holding compartment on the agricultural vehicle; and
a tire control system automatically controlling tire inflation pressure for the tires on the agricultural vehicle based on the detected fill level.

Example 34 is the agricultural system of any or all previous examples and further comprising:
a controllable tire inflation subsystem configured to adjust inflation pressure in the tires, wherein the tire control system is configured to identify a target inflation pressure for the tires based on the fill level and to control the controllable tire inflation subsystem based on the target inflation pressure.

Example 35 is the agricultural system of any or all previous examples wherein the tire control system comprises:
a tire inflation control system configured to detect a current inflation pressure in the tires and control the controllable tire inflation subsystem based on the current inflation pressure and the target inflation pressure.

Example 36 is the agricultural system of any or all previous examples wherein the tire control system comprises:
a load identification system configured to identify a load on the tires based on the fill level, the tire inflation control system being configured to identify the target inflation pressure for the tires based on the load on the tires.

Example 37 is the agricultural system of any or all previous examples wherein the tire control system comprises:
a material identification system configured to identify a type of material in the material holding compartment, the load identification system being configured to identify the load based on the fill level and the type of material.

Example 38 is the agricultural system of any or all previous examples wherein the load identification system is configured to identify a separate target inflation pressure corresponding to each of a plurality of different subsets of the tires and automatically control the tire inflation pressure by controlling the controllable tire inflation subsystem to adjust each of the different subsets of the tires based on the corresponding target inflation pressure.

Example 39 is a computer system, comprising:
at least one processor; and
a data store that stores computer executable instructions which, when executed by the at least one processor, cause the at least one processor to perform steps, comprising:
detecting a fill level of material in a material holding compartment on the agricultural vehicle;
identifying a target inflation pressure for the tires based on the fill level; and
controlling a controllable tire inflation subsystem to adjust inflation pressure in the tires to the target inflation pressure.

Example 40 is the computer system of any or all previous examples wherein identifying a target inflation pressure comprises:
identifying a load on the tires based on the fill level; and
identifying the target inflation pressure for the tires based on the load on the tires.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

As discussed above, there are a variety of different types of mobile work machines, such as agricultural machines. Agricultural machines include such things as row crop planters, air seeding carts, sprayers, tillage equipment with on-board fertilizer or cover crop systems, harvesters, grain carts, among others. These types of agricultural machines carry a load of material that varies during the operation of the agricultural machine.

For instance, row crop planters and air seeding carts often carry seeds that are planted during a planting operation. Therefore, the load carried by such agricultural machines varies during the planting operation, as seeds are moved from a tank to the ground. Other agricultural vehicles apply other materials to the ground. For instance, self-propelled or towed sprayers often have a tank that carries a liquid material, such as fertilizer, herbicide, pesticide, etc. As the sprayer travels through the field, the material in the tank is sprayed onto the field, and therefore, the load carried by the sprayer changes throughout the operation of the sprayer. Other application machines apply granular material or other material to the ground. For instance, tillage equipment may have a side dress bar or other mechanisms attached to it to apply fertilizer or other chemicals or materials to the field, during the operation of the tillage equipment.

Some harvesters harvest material (such as grain) and hold the harvested material in a tank. Such harvesters intermittently unload the material into grain carts or other carts that are often pulled by a tractor or other towing vehicle. Such harvesters can also unload the material into a semitrailer or other receiving vehicle. The load in the tank of such a harvester varies during the harvesting operation from empty to full as crop is harvested, and then to empty again, once the harvester unloads the material into a receiving vehicle. Other harvesters, such as forage harvesters, and sugar cane harvesters, unload the material, as it is harvested, into a receiving vehicle. The load in the receiving vehicle also varies during operation from empty to full, when it is loaded by the harvester, then to empty again, after the grain cart or other receiving vehicle is unloaded.

It can be seen that in all these examples, the load carried by the agricultural vehicle often varies over a field, during operation of the agricultural vehicle.

Figure 1:
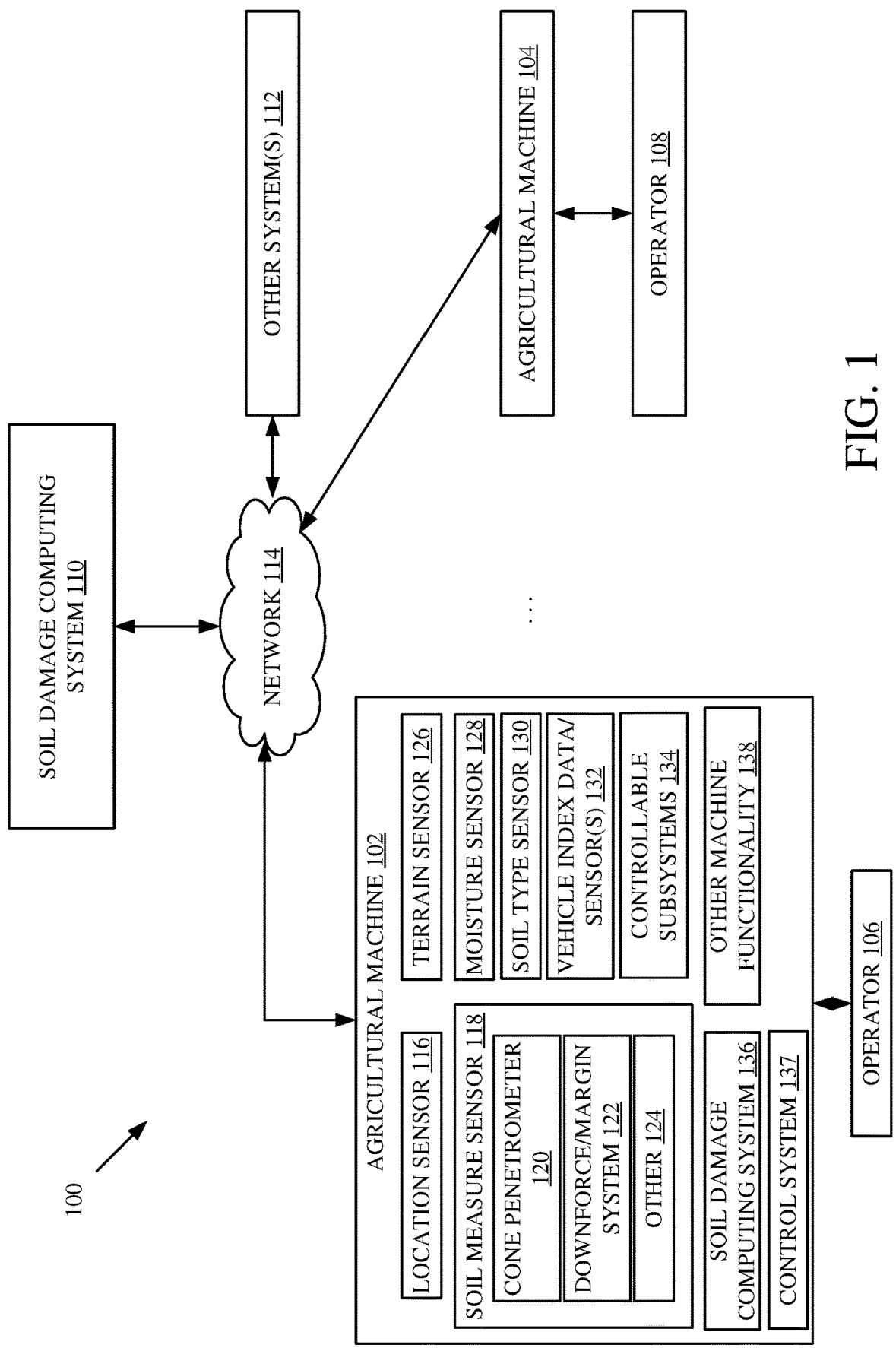
FIG. 1 is a block diagram of one example of an agricultural system.

FIG. 1 is a block diagram of one example of an agricultural system 100. Agricultural system 100 includes a set of agricultural machines 102-104 that are operated by operators 106-108, respectively. In the example shown in FIG. 1, a soil damage computing system 110 is shown communicating with agricultural machines 102-104, and other systems 112, over network 114. It will be noted that soil damage computing system 110 can be deployed on one or more of the agricultural machines 102-104 or on other systems 112 as well, but it is shown as a separate system that is accessed over network 114 by agricultural machines 102-104. System 110 can be distributed among various machines and locations as well.

Network 114 can be a local area network, a wide area network, a cellular communication network, a near field communication, or any of a wide variety of other networks or combinations of networks. The other systems 112 can be farm managers systems, vendor systems, manufacture systems, or any of a wide variety of other computing systems.

Agricultural machine 102 illustratively includes location sensor 116, soil measure sensor 118 (which can include cone potentiometer 120, downforce/margin system 122 and other items 124), terrain sensor 126, moisture sensor 128, soil type sensor 130, vehicle index data/sensors 132, controllable subsystems 134, soil damage computing system 136, control system 137, and other agricultural machine functionality 138. Agricultural machines 102-104 can be any of a wide variety of different types of agricultural machines. In some examples, machines 102-104 are machines that vary in weight as they travel over an agricultural field performing an agricultural operation. Such agricultural machines or vehicles can be agricultural machines, such as planting machines (which vary in weight based on seeding rate), material application systems (such as a sprayer which varies in weight as it applies material to a field), a harvester (which varies in weight at it harvests material in the field), and any of a wide variety of other machines. Location sensor 116 can be a global navigation satellite system (GNSS) receiver or another location sensor that senses the geographic location of agricultural machine 102. Such sensors can also include a dead reckoning system, or any of a wide variety of other sensors.

Terrain sensor 126 can sense the type of terrain (such as the terrain elevation, slope, etc.). Sensors 126 can be a gyroscopic sensor, an accelerometer, or any of a wide variety of other inertial measurement units, or terrain sensors that can sense the orientation of agricultural machine 102 as it travels through the field.

Moisture sensor 128 illustratively senses the moisture of the soil. Moisture sensor 128 can be a sensor probe mounted to machine 102 to engage the soil, or another sensor 128. Soil type sensor 130 is illustratively a sensor that senses the type of soil over which machine 102 is traveling. In one example, soil samples are taken and analyzed and then geographically correlated to the field. In other examples, soil type sensor 130 can be a sensor disposed on a different machine that samples and senses the soil type during a prior operation. Other soil type sensors can be used as well.

Soil measure sensor 118 generates a measure indicative of the ability of the soil to support a load. In one example, sensor 118 can be a cone penetrometer 120. Cone penetrometer 120 can be a mechanism that penetrates the soil during the operation of machine 102 and generates an output indicative of a cone index value. The cone index value for the soil is a measure of the resistance to penetration of the soil. Downforce/margin system 122 generates a proxy indicative of the cone index or otherwise indicative of the ability of the soil to bare a load. For instance, the downforce/margin system 122 can measure the downforce exerted by a row unit of a planter and reduce the measured downforce by the downforce margin which is the load borne by the gauge wheels of a row unit. This is indicative of the overall resistance imparted on the soil by the row unit and may be a proxy indicative of the cone index or otherwise indicative of the ability of the soil to bear a load.

Vehicle index data/sensors 132 sense a variable or other item that can be used to calculate a vehicle index indicative of the amount of force (e.g., in pounds per square inch or in other units) that machine 102 will exert on the soil as it travels over the soil. The vehicle index data/sensors 132 can be pre-stored data indicative of the weight of the machine, and indicative of how the weight of the machine will vary over its full-to-empty, or empty-to-full cycle. In another example, the data/sensors 132 can be sensors that sense the actual weight of the vehicle (such as load sensors in the axles of the vehicle, etc.) or another variable that is indicative of the force that the vehicle will impart to the ground as it travels over the field.

Controllable subsystems 134 on machine 102 can include such things as a vehicle navigation subsystem, a tire inflation subsystem, a load re-distribution subsystem, an operator interface subsystem, a traction control subsystem, a communication subsystem, a machine setting subsystem, among others. Soil damage computing system 136 can obtain the soil measure generated by soil measure sensor 118 indicative of the soils ability to support a load, and the vehicle index generated by vehicle index data/sensors 132 indicative of the force or load that machine 102 will apply to the soil. Based upon these values, soil damage computing system 136 can compute a soil damage metric indicative of a compaction of the soil, or other item of soil damage that will be imparted, or is being imparted, by machine 102 as machine 102 is traveling over the field.

It will be noted that soil damage computing system 136 need not necessarily reside on agricultural machine 102, but can be separate from machine 102 (as indicated by soil damage computing system 110) and accessed over network 114. In one example, soil damage computing system 136 or 110 can generate a near real time soil damage metric indicative of the soil damage (if any) being imparted by machine 102 on the soil over which it is traveling. In another example, the soil damage computing system 136, 110 can generate a predictive value indicative of the predicted soil damage that machine 102 will impart on the soil if it travels over the soil in the future.

Based on the soil damage metric, control system 137 can generate control signals to control the controllable subsystems 134. For instance, where the soil damage metrics indicate a relatively large degree of soil damage (compared to a threshold value input by the user or a default threshold or another threshold), control system 137 can generate control signals to control the tire inflation subsystem to deflate the tires to increase the contact patch between the tire and the ground, and thus to spread the force imparted by machine 102 on the soil over a large area. In another example, control system 137 can generate control signals to output a display or other operator output that can be used to notify the operator of the level of damage that is being, or will be, imparted on the soil. In yet another example, control system 137 can control a navigation system to engage a path planning system to generate a recommended path through the field that will reduce the overall damage to the soil. For instance, the path planning system may generate a path that has machine 102 traveling over particularly susceptible spots in the field (such as low spots, muddy spots, etc.) when machine 102 is closer to empty than full so that machine 102 is imparting less force on the field. In another example, the path planning system may plan a path that avoids the vulnerable areas until later in the day (such as when they dry out), etc. These are just examples and other examples are contemplated herein as well. In yet another example, control system 137 can communicate the soil damage metric to other agricultural machines 104, to other systems 112, etc.

Figure 2:
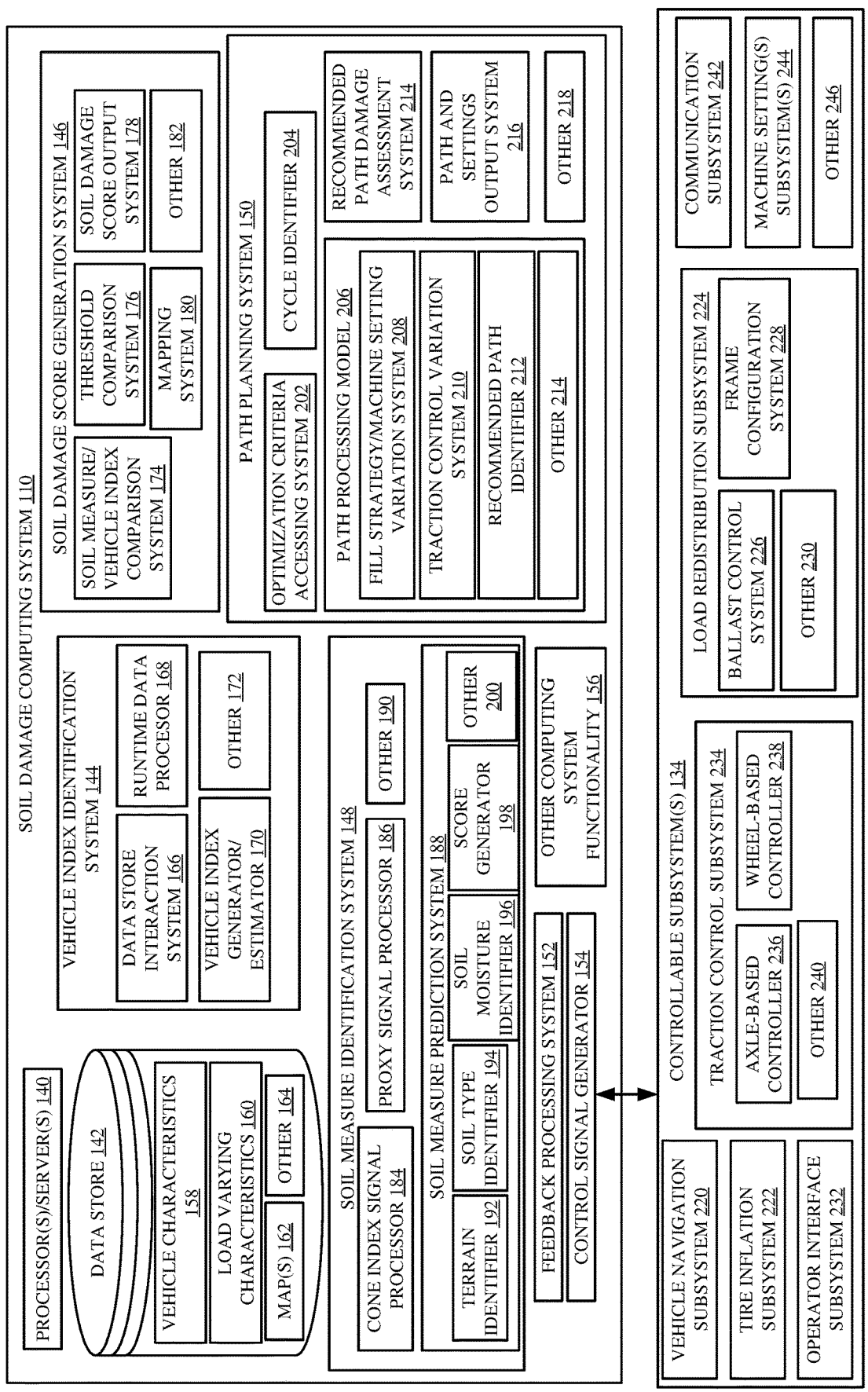
FIG. 2 is a block diagram showing one example of a soil damage computing system.

FIG. 2 is a block diagram showing one example of the soil damage computing system in more detail. For purposes of the present discussion, it will be assumed that soil damage computing system 110 is being shown and described in FIG. 2. Also, soil damage computing systems 110 and 136 can be similar or different. For purposes of the present description it will be assumed that they are similar so that only soil damage computing system 110 is described in more detail.

FIG. 2 shows that, in one example, soil damage computing system 110 can include one or more processors or servers 140, data store 142, vehicle index identification system 144, soil damage score generator system 146, soil measure identification system 148, path planning system 150, feedback processing system 152, control signal generator 154, and other computing system functionality 156. Data store 142 can store vehicle characteristics 158, load varying characteristics 160, maps 162, and other items 164. Vehicle index identification system 144 can include data store interaction system 166, runtime data processor 168, vehicle index generator/estimator 170, and other items 172. Soil damage score generation system 146 can include soil measure/vehicle index comparison system 174, threshold comparison system 176, soil damage score output system 178, mapping system 180, and other items 182.

Soil measure identification system 148 can include cone index signal processor 184, proxy signal processor 186, soil measure prediction system 188, and other items 190. Soil measure prediction system 188 can include terrain identifier 192, soil type identifier 194, soil measure identifier 196, score generator 198, and other items 200. Path planning system 150 can include optimization criteria accessing system 202, cycle identifier 204, and path processing model 206 (which can include fill strategy/machine setting variation system 208, traction control variation system 210, recommended path identifier 212, and other items 214). Path planning system 150 can include recommended path damage assessment system 214, suggested path and settings output system 216, and other items 218.

FIG. 2 also shows that controllable subsystems 134 can include vehicle navigation subsystem 220, tire inflation subsystem 222, load redistribution subsystem 224 (which can include ballast control system 226, frame configuration system 228, and other items 230), operator interface subsystem 232, traction control subsystem 234 (which can include axel-based controller 236, wheel-based controller 238 and other items 240), communication subsystem 242, machine settings subsystem 244, and other items 246. Before describing soil damage computing system 110, and its operation, in more detail, a description of some of the items in soil damage computing system 110, and their operation, will first be provided.

Vehicle characteristics 158 can include the physical dimensions of the vehicle, the weight of the vehicle, the model and make of the vehicle, among other things. Load varying characteristics 160 can be data indicative of how the load carried by the vehicle varies throughout its full-to-empty or empty-to-full cycle. For instance, load varying characteristics may include a lookup table, a curve, or other model or data that indicate how quickly the load of a seeding machine drops as it is seeding at a particular seed population rate, at a particular ground speed, etc. The load varying characteristics 160, in another example, indicate how the load of a harvester increases as it is harvesting a particular hybrid, with a moisture level, in a field that has a particular estimated yield, at a particular harvester speed, etc. These are examples only and a wide variety of other models, data structures, or mechanisms can be used to indicate that load varying characteristics 160 of a vehicle. Maps 162 may include terrain maps, soil type maps, yield maps, soil measure maps, soil damage maps, moisture maps, vehicle index maps, or other maps that indicate characteristics of the field, characteristics of the machine as those characteristics vary over the field, or other information.

Vehicle index identification system 144 generates the vehicle index which indicates the amount of force that the vehicle or machine 102 will exert on the soil over which it is traveling. Data store interaction system 166 can interact with data store 142 to obtain the vehicle characteristics 158 and/or the load varying characteristics 160 and/or maps 162. Runtime data processor 168 can obtain runtime information from vehicle index data/sensors 132 that may be used to derive the vehicle index value for machine 102. Vehicle index generator/estimator 170 can then either generate the vehicle index value, or estimate that value, based upon the information obtained. For instance, when runtime data processor 168 is generating data indicative of how the load of the vehicle is changing over time, vehicle index generator 170 can use that information in conjunction with the vehicle characteristics 158 and/or other information to generate a vehicle index value indicative of the actual load being imparted on the soil by the agricultural machine. When the information is indicative of how the load of the vehicle will change in the future during its empty-to-full or full-to-empty cycle, then vehicle index generator/estimator 170 can estimate the vehicle index value at a time in the future, or at a location in the field, etc.

Soil measure identification system 148 generates a soil measure value indicative of the ability of the soil to bear a load. Cone index signal processor 184 can receive the signal from cone penetrometer 120 and process that signal to obtain a cone index value indicative of the cone index value for the soil sensed by cone index penetrometer 120. Proxy signal processor 186 can receive the signal from a proxy of the cone index (e.g., from downforce/margin system 122) and process that signal to identify the soil measure value from the proxy signal.

Soil measure prediction system 188 can generate a prediction of the soil measure at different points over the field, based upon the information generated by a plurality of different sensors, or generated in other ways. For instance, terrain identifier 192 can identify the type of terrain 1 in the field based on a signal from terrain sensor 126 (shown in FIG. 1) or may obtain the terrain information from maps 162 or in other ways. Soil type identifier 194 can obtain a soil type at different locations in the field from a soil type sensor 130 or from soil maps 162 or in other ways. Soil moisture identifier 196 can obtain the soil moisture values for soil at different locations in the field from moisture sensor 128 or from soil moisture maps 162 or in other ways. For instance, based upon the terrain, soil moisture identifier 196 may identify low spots. Based on weather information, such as precipitation information, sun information, temperature information, wind information, etc. soil moisture identifier 196 can estimate soil moisture at different locations in the field. Score generator 198 can generate the soil measure value indicative of the ability of the soil to bear a load based upon the information from identifiers 192, 194, 196, and/or other information generated by other items 200.

Soil damage score generation system 146 obtains the vehicle index from vehicle index identification system 144 and the soil measure from soil measure identification system 148 and generates a soil damage score which can be used by path planning system 150 and/or control signal generator 154 to generate control signals for controlling controllable subsystem 134.

Soil measure/vehicle index comparison system illustratively converts the soil measure and the vehicle index to comparable units (such as pounds per square inch, etc.) and compares the soil measure to the vehicle index to determine whether the vehicle will damage the soil. For instance, if the vehicle index exceeds the soil measure, this means that the force that the vehicle will exert on the soil exceeds the ability of the soil to bear a load, and thus will result in compaction. However, some compaction may be acceptable. Therefore, threshold comparison system 176 determines whether the amount by which the vehicle index exceeds the soil measure meets a threshold level. The threshold level may indicate when undesirable soil damage occurs. The threshold level may be input by the operator, it may be empirically determined, it may be a default or dynamically changing value, among other things.

Mapping system 180 can generate a map of the soil damage scores. The map may be of scores from actual sensed values, or a predictive map that predicts the soil damage scores based upon the load variation of the agricultural machine as it travels over the field (and thus based on its varying vehicle index values) and based upon the predicted soil measures of the soil in the field generated by soil measure prediction system 188. The soil damage scores can be stored in maps or in other ways as well and soil damage score output system 178 can generate an output indicative of the soil damage scores. For instance, soil damage score output system 178 may provide an output to path planning system 150 and/or control signal generator 154. Soil damage score output system 178 can provide an output to other computing system functionality 156 as well.

Path planning system 150 can receive the output from soil damage score output system 178 and perform path planning to identify paths that the machine should take through the field when performing its operation. In another example, path planning system 150 may generate a timing or scheduling output indicative of when the machine should perform its path or other outputs as well.

Optimization criteria accessing system 202 identifies the optimization criteria that are to be used in path planning. For instance, the optimization criteria may be stored in data store 142 or elsewhere. The optimization criteria may be input by the operator, or they may be default criteria. The optimization criteria may be dynamically changed or set in other ways. By way of example, it may be that the path planning system is to calculate a path for the agricultural machine through the field optimizing productivity. In another example, the path may be calculated optimizing the soil damage score (to reduce soil damage wherever possible). The optimization criteria may be to plan the agricultural operation to take place as quickly as possible, thus optimizing speed. The optimization criteria accessing system 202 may access optimization criteria in other ways, and those criteria may be other criteria as well.

Cycle identifier 204 identifies the full-to-empty cycle of the agricultural machine (or the empty-to-full cycle where appropriate). Identifier 204 may identify the distance that the machine can travel during the cycle, the time the machine will take to travel over that cycle, or other characteristics or parameters of the full-to-empty cycle or the empty-to-full cycle of the agricultural machine. Once the optimization criteria are known, and the cycle of the agricultural machine is known, then path processing model 206 performs path processing to identify a recommended path through the field for the agricultural machine.

Path processing model 206 can be any type of model that generates a path output to optimize the optimization criteria. In generating the path, model 206 varies different variables, such as the geographic location of the path, the traction control that is used, the fill strategy and machine settings that are used by the machine (such as how full the machine is filled and when it is unloaded during different paths, etc.), among other things. By way of example, fill strategies/machine settings variation system 208 varies the fill strategies and machine settings so that path processing model 206 can model paths, optimizing on the optimization criteria, with different fill strategies in different machine settings. Traction control variation system 210 varies the traction control strategies or settings that are used to control traction on the machine so that model 206 can model different paths through the field, optimizing based upon the optimization criteria, using different traction control settings or traction control strategies. Other items can be varied so that model 206 can model different paths through the field with other variations as well. Recommended path identifier 212 identifies the recommended path, with a recommended fill strategy and set of machine settings, as well as traction control variations that were modeled.

Recommended path damage assessment system 214 then analyzes the recommended path to access the soil damage that will be created by the machine, if it follows the recommended path. For instance, it may be that path processing model 206 outputs the recommended path, but even the recommended path may cause an undesirable amount of damage. Therefore, system 214 assesses the soil damage that will be inflicted by the machine, and can generate an output indicative of the damage. Recommended path and settings output system 216 then generates an output indicative of the recommended path and the recommended settings (e.g., fill strategy, machine settings, traction control strategy and settings, etc.).

System 216 can also output an indication of the damage that will be inflicted, as determined by recommended path damage assessment system 214. System 216 may output the recommended path as a navigational path indicating the geographic path that the machine is to take in order to follow the recommended path. The recommended path can be output to a navigation system which can automatically navigate the machine along the path, or it can be output to an operator so that the operator can manually navigate the machine over that path, or it can be output in other ways. Similarly, the recommended settings can be output so that they can be automatically set on the machine or set by an operator, etc.

Control signal generator 154 can receive the recommended path and settings output by system 216 and generate control signals to control controllable subsystems 134 based upon the recommended path and settings. For instance, control signal generator 154 can generate output signals to control vehicle navigation subsystem 280 to automatically navigate the agricultural machine through the recommended path. Where the settings include tire inflation settings, then control signal generator 154 can generate control signals to control tire inflation subsystem 222 to automatically inflate and deflate the tires, as the agricultural machine travels along the recommended path, based upon the tire inflation settings.

It may also be that the recommended settings are settings for a load redistribution subsystem 224 that can be used to redistribute the load on the agricultural machine about its frame. Therefore, control signal generator 154 can generate control signals to accomplish the desired load redistribution using subsystem 224. By way of example, it may be that the agricultural vehicle is configured with a ballast control signal system 226 that can mechanically move ballast about the agricultural machine to change where the load imparted by the machine is imparted to the soil over which it is traveling. Control signal generator 154 can generate control signals to control ballast control system 226 to redistribute the ballast on the machine based upon the recommended settings. Frame configuration system 228 can be controlled to reconfigure the frame of the agricultural machine, such as to collapse the machine, expand the machine, etc., to change the way the load from the machine is imparted to the field over which it is traveling. The frame configuration system 228 can use hydraulic or pneumatic cylinders or other electrical, mechanical, pneumatic, hydraulic, or other actuators to change the configuration of the machine frame. The control signals generated by control signal generator 154 can be used to control those actuators to move the frame to a desired configuration.

Traction control system 234 can use axel-based controllers 236 to control the torque applied by individual axels on the agricultural machine. Wheel-based controller 238 can be used to control the torque applied by individual wheels or individual tracks or other individual ground engaging mechanisms. Therefore, control signal generator 154 can generate control signals to control the axel-based controller 236 and/or the wheel-based controller 238 to perform traction control on the agricultural vehicle based upon the recommended settings.

Operator interface subsystem 232 can include any operator interface subsystems that the operator 106 can use to control agricultural machine 102, such as a steering wheel, joysticks, levers, linkages, pedals, buttons, a touch sensitive display screen or another display screen, a microphone and speaker (where speech synthesis and speech recognition are used), or a wide variety of other audio, visual, and haptic user interface elements. Operator interface subsystem 232 can thus display or otherwise communicate the recommended path and settings to the operator and thus control signal generator 154 can generate control signals to control operator interface subsystem 232 to perform that type of communication with the operator.

Communication subsystem 242 can be controlled to communicate the recommended path and settings to other systems 112, other agricultural machines 104, etc. Machines setting subsystem 246 can be used to automatically set the machine settings to the suggested settings. Therefore, control signal generator 154 can generate control signals to control machine settings subsystem 244 to set the machine settings to the recommended settings.

Figure 3:
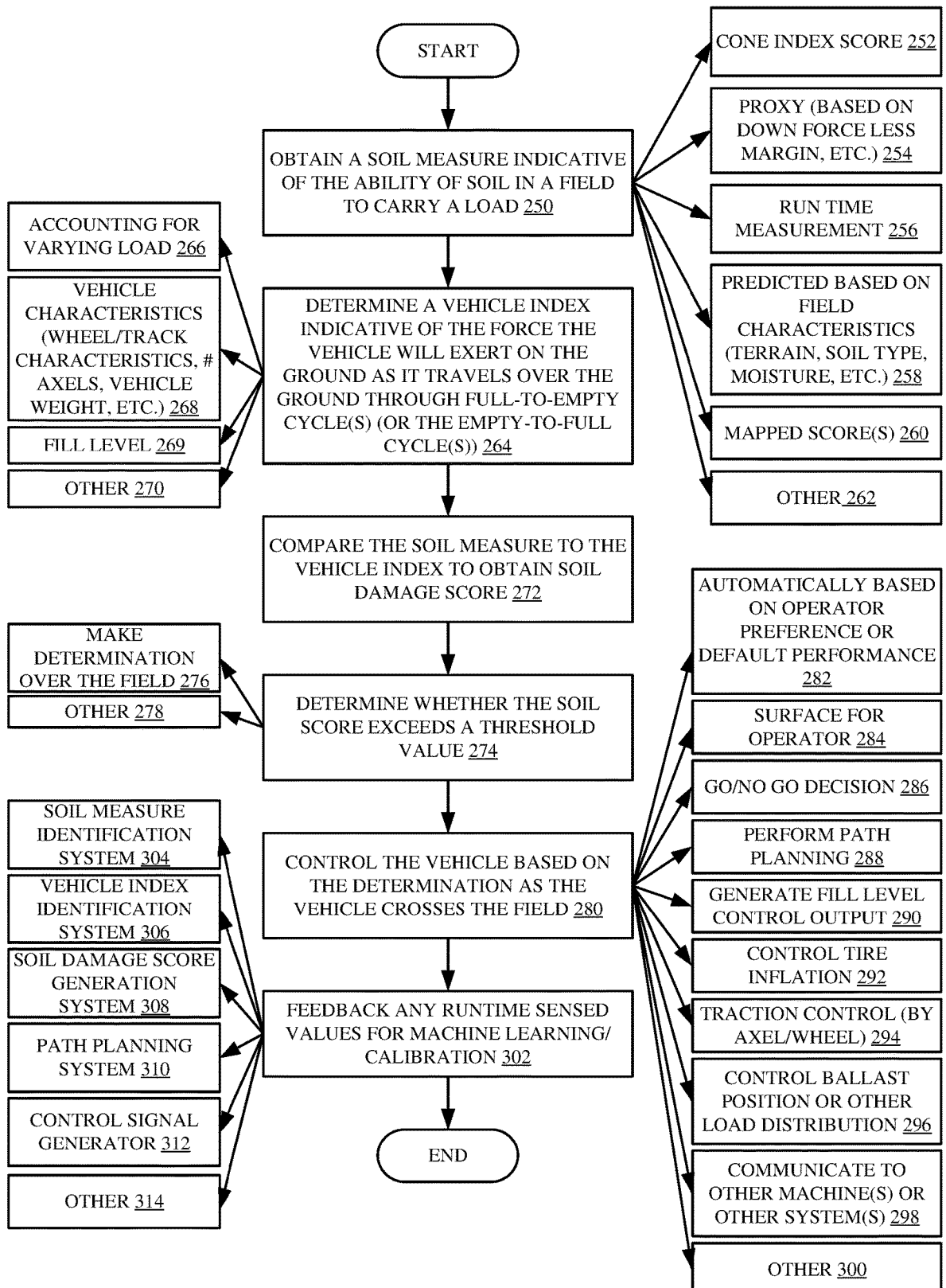
FIG. 3 is a flow diagram illustrating one example of the overall operation of an agricultural system.

FIG. 3 is a flow diagram illustrating one example of the overall operation of the agricultural system 100, in controlling agricultural machine 102 based upon a soil damage score that is calculated by soil damage score generation system 146. Soil damage score generation system 146 obtains a soil measure indicative of the ability of the soil in a field to carry a load from soil measure identification system 148. Obtaining the soil measure is indicated by block 250 in the flow diagram of FIG. 3. The soil measure can be a cone index score 252, a proxy 254, such as a signal based on the downforce, less the downforce margin, etc. The soil measure can be based on a runtime measurement taken (such as from a cone penetrometer 120, as indicated by block 256) or the soil measure can be a predicted value based upon field characteristics, such as the terrain, soil type, moisture, etc., as indicated by block 258. The soil measure may be a map of soil measure scores through the field, as indicated by block 260, or it can be provided in a wide variety of other ways, as indicated by block 262.

Soil damage score generation system 146 then determines a vehicle index. The vehicle index can account for the variation in the load based upon the load varying characteristics 160 in data store 142, or in other ways. For instance, system 146 can obtain the vehicle index from vehicle index identification system 144. The vehicle index is indicative of the force that the vehicle will exert on the ground as the vehicle travels over the ground through the full-to-empty cycle or the empty-to-full cycle, as indicated by block 264 in the flow diagram of FIG. 3. The vehicle index identification system 144 can generate the vehicle index accounting for the varying load that the vehicle will carry as it travels over the field, as indicated by block 266. The vehicle index can take into account the vehicle characteristics 158, as indicated by block 268, the fill level of the vehicle, as indicated by block 269, and other items as indicated by block 270. Soil measure/vehicle index comparison system 174 then compares the soil measure to the vehicle index to obtain a soil damage score, as indicated by block 272. Threshold comparison system 176 determines whether the soil damage score exceeds a threshold value, as indicated by block 274. Mapping system 180 can generate the soil damage score over the entire field, as indicated by block 276, and the soil damage score can be compared against a threshold in other ways as well, as indicated by block 278.

Control signal generator 154 can then generate control signals to control subsystems 134 of the agricultural machine, as it crosses the field. Controlling the vehicle is indicated by block 280 in the flow diagram of FIG. 3. The vehicle can be controlled automatically or based on operator preference or default values, as indicated by block 282. The soil damage scores can be surfaced for the operator, as indicated by block 284, and control signal generator 154 can make a go/no go decision and surface that for the operator through operator interface subsystem 282, as indicated by block 286. For instance, control signal generator 154 may determine that the damage scores are so high that the machine should not perform the agricultural operation until a later time when the soil stabilizes, or firms up, or under other circumstances. This can be displayed for the user, or otherwise surfaced for the user, through an operator interface subsystem 232.

Path planning system 150 can perform path planning based on the damage scores, as indicated by block 288. The path processing model 206 can generate a recommended fill strategy, as indicated by block 290, and that recommended fill strategy can be output to the operator or to the machine for automatic control as well.

Tire inflation subsystem 222 can be controlled to control the tire inflation based upon the soil damage scores, as indicated by block 292. Traction control system 234 can be controlled to control the traction control on an individual axel basis or on an individual wheel basis, as indicated by block 294. Load redistribution subsystem 224 can be controlled to control the ballast position or other load distribution, as indicated by block 296. Communication subsystem 242 can be used to communicate the recommended path, the soil damage scores, the recommended machine settings, etc., to other machines or other systems, as indicated by block 298. The machine can be controlled in a wide variety of other ways as well, as indicated by block 300.

It should also be noted that, in one example, the values that have been estimated or predicted by soil damage computing system 110 can be modified by feedback processing system 152 which may obtain actual, measured values and perform machine learning on the various functionality in soil damage computing system 110 that generates estimates or predictions to improve the accuracy of those estimates or predictions. Similarly, estimated or predicted values can be modified or calibrated by feedback processing system 152 based upon actual measured values as well. Feeding back any runtime sensed values for machine learning and/or calibration is indicated by block 302 in the flow diagram of FIG. 3. For instance, where soil measure prediction system 188 predicts a cone index value or other soil measure, then a measured cone index value may be fed back, for processing by feedback processing 152 so that the algorithm used by soil measure prediction system 188 can be trained using machine learning or other techniques for more accuracy. Also, other predicted values can be modified or calibrated to improve their accuracy based on the actual, measured value(s). Performing feedback to the soil measure identification system is indicated by block 304 in the flow diagram of FIG. 3.

Also, in an example in which vehicle index generator/estimator 170 generates an estimated value for the vehicle, a vehicle index sensor 132 may sense the actual vehicle index value (such as the weight of the vehicle, etc.). The actual sensed value may be fed back to feedback processing system 152 for processing using machine learning or other algorithms to improve the estimation generated by vehicle index generator/estimator 170. Estimated values can be calibrated based on the fed back values as well. Feeding the information back for improving the accuracy of vehicle index identification system 144 is indicated by block 306 in the flow diagram of FIG. 3.

These or other measured values may also be fed back to soil damage score generation system 146 to improve the accuracy of that system, as indicated by block 308. Measured values can also be fed back to path planning system 150 to improve the path planning as indicated by block 310.

For instance, where path planning system 150 generates a recommended path and recommended settings, those settings and the characteristics of the path can be sensed and fed back to path planning system 150 for machine learning to improve path planning and recommended settings. The measured values can be processed by feedback processing system 152 to improve the control signals generated by control signal generator 154 as well, as indicated by block 312. Measured values can be fed back in other ways, for use by other machine learning or calibration algorithms as well, as indicated by block 314.

Figure 4:
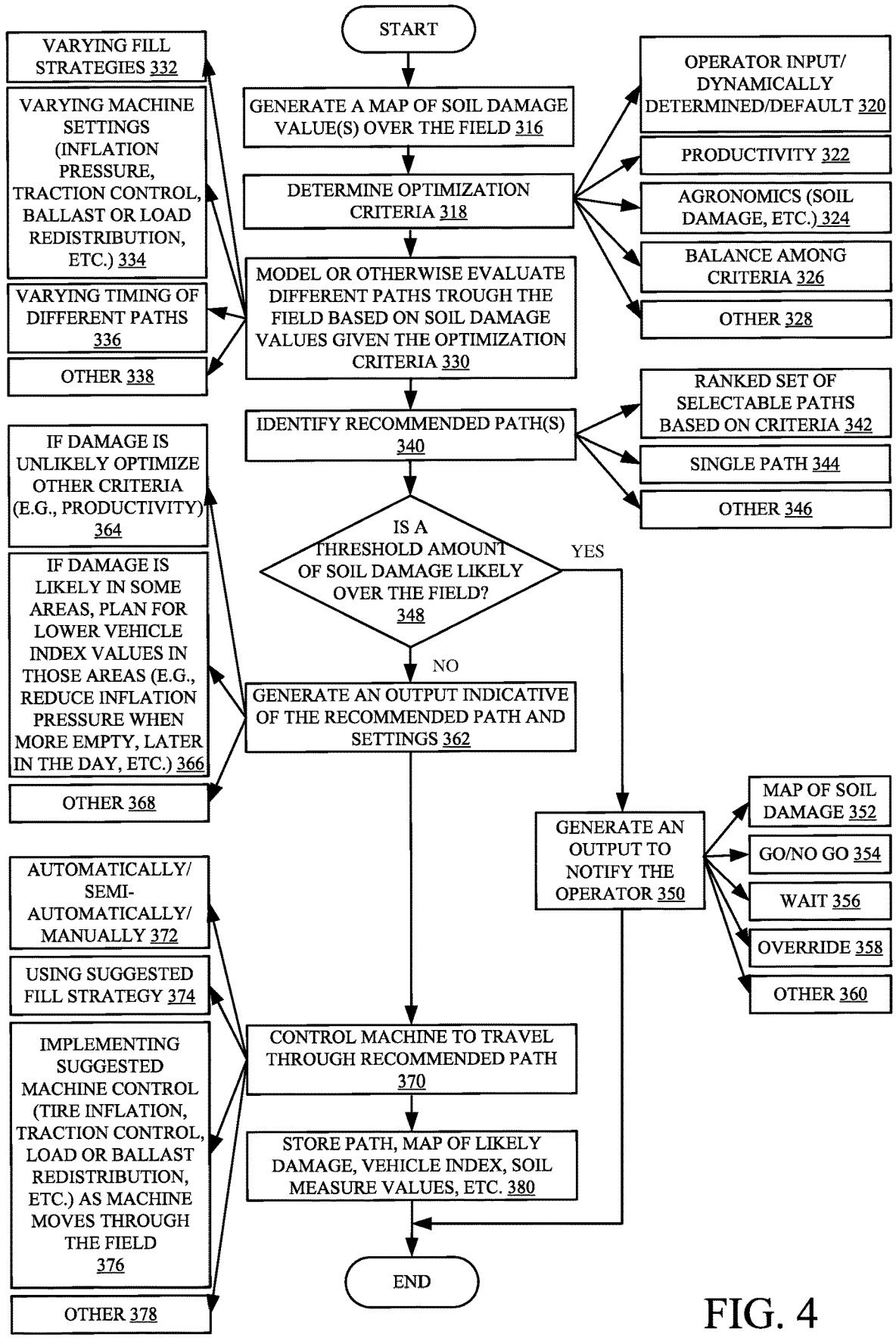
FIG. 4 is a flow diagram illustrating one example of the operation of a path planning system in generating a path plan based upon a soil damage score.

FIG. 4 is a flow diagram illustrating one example of the operation of path planning system 150, in more detail. It is first assumed that soil damage score generator system 146 uses mapping system 180 to generate a map of soil damage values over the field upon which the machine will be performing in agricultural operation. Generating a map of the soil damage values over the field is indicated by block 316 in the flow diagram of FIG. 4. Optimization criteria accessing system 202 then determines the optimization criteria that are to be used by path planning system 150 in identifying a recommended path. Determining the optimization criteria is indicated by block 318 in the flow diagram of FIG. 4. The optimization criteria may be determined based on an operator input, the optimization criteria may be determined dynamically, or the optimization criteria may be default values that are obtained from data store 142, as indicated by block 320. The optimization criteria may be productivity 322, or agronomics (such as soil damage) 324. The optimization criteria may call for a balance between productivity and agronomics, as indicated by block 326. The optimization criteria may be other criteria and they may be obtained in other ways as well, as indicated by block 328.

Path processing model 206 then models or otherwise evaluates different paths through the field based on the soil damage values given the optimization criteria, as indicated by block 330. The different paths may be evaluated by varying the fill strategies as indicated by block 332 and by varying the machine settings (such as tire inflation pressure, traction control, ballast or load redistribution, etc.), as indicated by block 334. The various paths through the field can be evaluated based on the optimization criteria by varying the timing when the agricultural machine will be at different points in the field, as indicated by block 336. The different paths can be modeled or evaluated by varying a wide variety of other parameters, and in a wide variety of other ways, as indicated by block 338.

Recommended path identifier 212 then identifies on or more recommended paths, as indicated by block 340. In one example, recommended path identifier 212 identifies a plurality of different recommended paths that are ranked based on the optimization criteria, and are output as different selectable paths. Outputting the ranked paths as different selectable paths based on the optimization criteria is indicated by block 342. Recommended path identifier 212 may output the recommended path as a single path, as indicated by block 344, or in other ways, as indicated by block 346.

Recommended path damage assessment system 214 then determines whether a threshold amount of soil damage is likely over the field if the vehicle follows the recommended path. Again, the threshold can be input by the operator, it can be a default threshold, or it can be a dynamically determined threshold or another threshold. Determining whether a threshold amount of soil damage is likely over the field is indicated by block 348 in the flow diagram of FIG. 4.

If so, then an indication that the threshold amount of soil damage is likely to occur is output to control signal generator 154 which generates an output on operator interface subsystem 232 notifying the operator that a threshold amount of damage will occur over the field, as indicated by block 350. The output may be a map of the likely soil damage, as indicated by block 352, or the output can be a simple go/no go indicator indicating that the agricultural operation should not be performed at this time, as indicated by block 354. The output may be an indication that the operation should be delayed for a certain amount of time, as indicated by block 356. The output may include an override actuator so that the operator can override the output, as indicated by block 358, and then continue to perform the agricultural operation. The output notifying the operator can be any of a wide variety of other outputs notifying the operator in other ways as well, as indicated by block 360.

Assuming that a threshold amount of soil damage is not likely to occur over the field when navigating through the recommended path, then the recommended path and settings output system 216 generates an output indicative of the recommended path and recommended settings, as indicated by block 362. In one example, if damage is unlikely, then the recommended path is optimized based on criteria other than damage, such as productivity, as indicated by block 364. If the damage is likely in some sensitive areas, then the recommended path is illustratively a path which plans to have the agricultural vehicle traveling over those sensitive areas when it has a lower vehicle index. This may include reducing the tire inflation pressure over those areas, it may include driving the vehicle over those areas when the vehicle is less full than at other times, or it may include having the vehicle travel over those areas later in the day so that the areas have a chance to dry out, and firm up, etc., as indicated by block 366. The output of the recommended path and settings may be generated in other ways as well, as indicated by block 368. Control signal generator 154 receives the recommended path and settings output by system 216 and generates control signals to control controllable subsystems 134 so that the agricultural machine travels through the recommended path, as indicated by block 370. In one example, the control signals can be applied to vehicle navigation system 220 to automatically control the vehicle to travel through the recommended path. In another example, the control signals can control the vehicle navigation subsystem 220 to travel through the recommended path semiautomatically (such as controlling the vehicle automatically during a pass through the field and controlling the vehicle manually during turns), or the control signal generator 154 can generate control signals to control operator interface subsystem 232 so that the operator can manually control the agricultural vehicle to travel over the recommended path. Controlling the agricultural vehicle to travel automatically, semiautomatically, or manually over the recommended path is indicated by block 372 in the flow diagram of FIG. 4.

The control signal generator 154 can control controllable subsystems 134 to implement a suggested fill strategy (such as to fill the machine partially full, to unload the machine with material to be applied after the machine is only partially full during harvesting, or to employ other fill strategies), as indicated by block 374. Similarly, control signal generator 154 can generate control signals to control the controllable subsystems 134 to implement other desired machine control, such as to control tire inflation pressure, traction control, load or ballast redistribution, etc., as the agricultural machine moves through the field over the recommended path, as indicated by block 376. The control signal generator 154 can generate control signals in other ways to perform other control operations as well, as indicated by block 378.

In one example, soil damage computing system 110 then stores the recommended path, the map of the likely soil damage values, the vehicle index and soil measure values, and any other desired values or information corresponding to the recommended path, as indicated by block 380. The information can be stored in data store 142 or in other systems.

Figure 5:
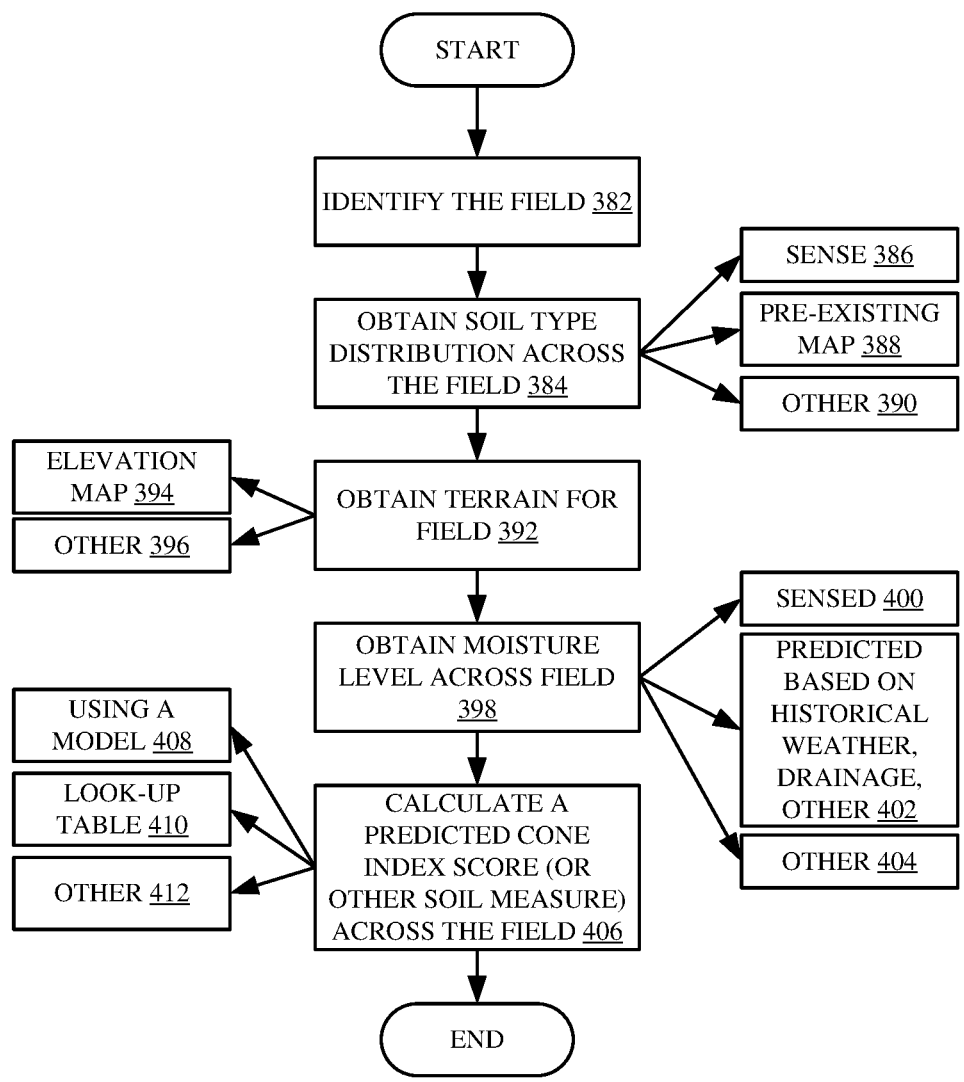
FIG. 5 is a flow diagram illustrating one example of the operation of a soil measure identifying system in predicting a soil cone index or similar measure.

FIG. 5 is a flow diagram illustrating one example of the operation of soil measure prediction system 188 in predicting a soil measure (such as a cone index) for different geographic areas of a field. Soil measure prediction system 188 first identifies the field for which the cone index values are to be predicted, as indicated by block 382 in the flow diagram of FIG. 5.

Soil type identifier 194 then obtains the soil type distribution across the field, as indicated by block 384. The soil type can be sensed by a sensor as indicated by block 386 or it can be obtained from a preexisting map as indicated by block 388, or the soil type can be obtained in other ways as well, as indicated by block 390. Terrain identifier 192 then obtains terrain indicators indicating the terrain (e.g., slope, elevation, etc.) across the field, as indicated by block 392. The terrain can be obtained from an elevation map 394, the terrain can be sensed, or the terrain can be obtained in other ways, as indicated by block 396.

Soil moisture identifier 196 then obtains a moisture level of the soil across the field, as indicated by block 398. The soil moisture level can be sensed by soil moisture sensors, as indicated by block 400, or the soil moisture can be predicted based on historical weather information (such as precipitation information), drainage, and other information, as indicated by block 402. The soil moisture level across the field can be obtained in other ways as well, as indicated by block 404. Score generator 198 then calculates a predicted cone index score (or another soil measure indicative of the ability of the soil to support a load) across the field, as indicated by block 406. Score generator 198 can use a score generation model 408, a lookup table, 410, or any of a wide variety of other mechanisms for calculating a predictive cone index or other soil measure score across the field, based upon the soil type, the terrain, the moisture level and/or any other characteristics, as indicated by block 412.

Figure 6:
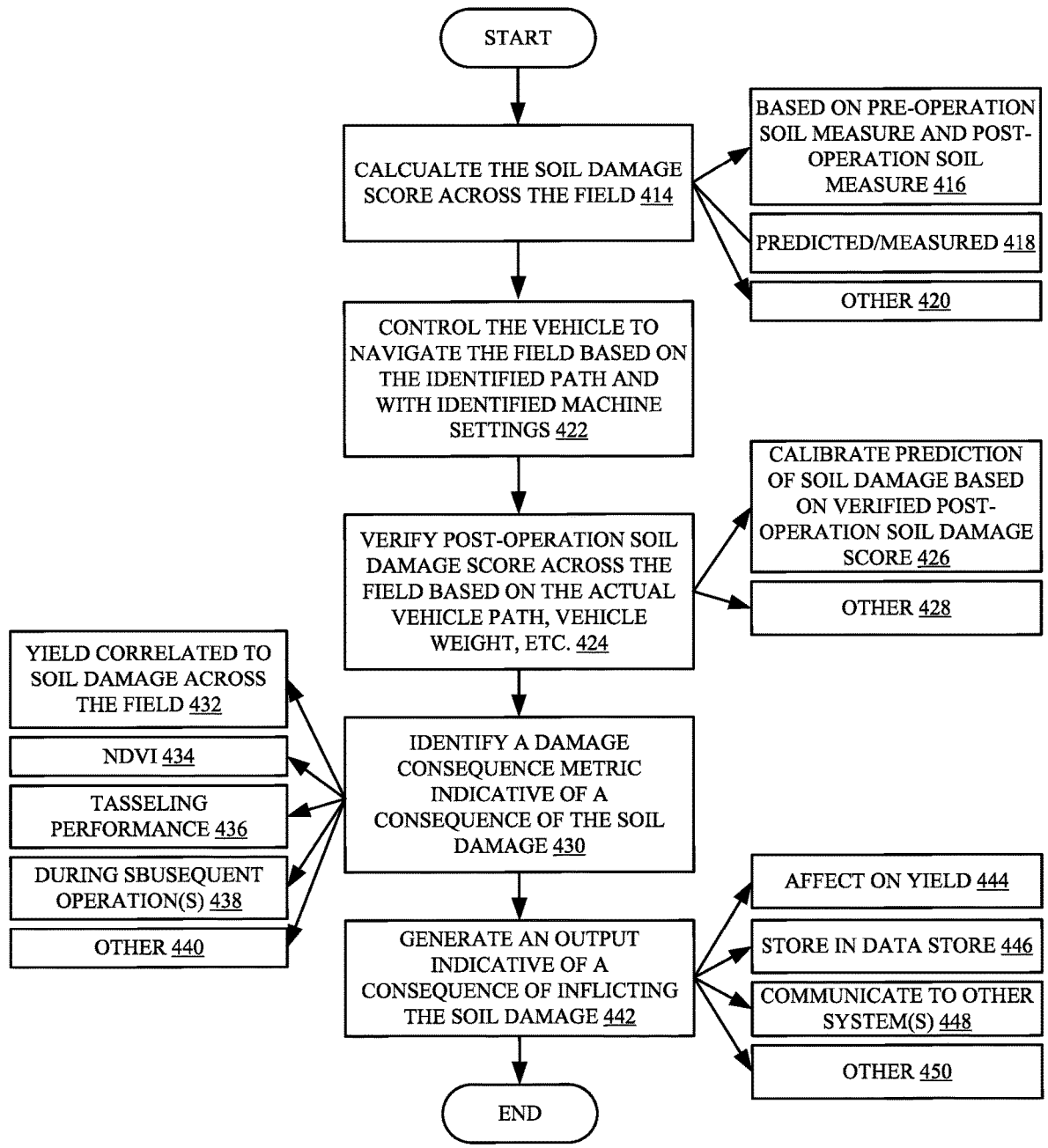
FIG. 6 is a flow diagram illustrating one example of the operation of the soil damage computing system in correlating a soil damage score to a consequence, such as a change in productivity.

FIG. 6 is a flow diagram illustrating one example of how soil damage computing system 110 generates an output indicating the consequences of inflicting predicted or estimated soil damage on the field. If the operator is provided with the potential consequences for inflicting the damage, then the operator may be able to make a more informed choice as to whether to perform the operation, as planned. It is first assumed that soil damage score generation system 146 calculates the soil damage score across the field, as indicated by block 414 in the flow diagram of FIG. 6. The soil damage score may be based on the soil measure calculated by soil measure identification system 148 prior to performing the operation. Also, the soil damage score can be an actually measured score based on the soil measure prior to performing the agricultural operation and the soil measure after performing the operation, as indicated by block 416. The soil damage score across the field can be predicted or measured as indicated by block 418, or it can be calculated in other ways as well, as indicated by block 420.

In the example shown in FIG. 6, control signal generator 154 controls the agricultural machine to travel through the field based on the identified path, with the identified machine settings. Navigating the machine along the recommended path with the machine settings is indicated by block 422 in the flow diagram of FIG. 6. The agricultural machine illustratively is fitted with a cone index penetrometer or another device that can be used to detect the soil measure and vehicle index so that the soil damage score for the different geographic locations in the field can be verified using actual measurements. Verifying the post-operation soil damage score across the field based on the actual vehicle path, the vehicle weight, the soil measure, etc., is indicated by block 424 in the flow diagram of FIG. 6.

The verified soil damage score can be used to calibrate the soil damage score generation system in generating the soil damage score. The verified soil damage score can also be used to calibrate the soil measure prediction system 188 so that the soil measure can be calibrated as well. Calibrating the predicted soil damage score and soil measure based upon the verified post-operation soil damage score is indicated by block 426. The post-operation soil damage score can be obtained in other ways, and used for other processing as well, as indicated by block 428.

Soil damage score output system 178 then identifies a consequence of the damage, as a damage consequence metric, indicative of the consequence of the soil damage. Generating a damage consequence metric is indicated by block 430 in the flow diagram of FIG. 6. For example, the yield can be correlated to the soil damage score across the field to identify a yield loss in areas of the field that are more highly damaged. Identifying the damage consequence metric as the yield correlated to soil damage across the field is indicated by block 432 in the flow diagram of FIG. 6. The damage consequence metric can be correlated to plant health as indicated by normalized difference vegetation index (NDVI) data corresponding to the field, as indicated by block 434.

The damage consequence metric can be a metric that correlates the tasseling performance of corn (or other vegetation performance characteristic) to the soil damage score across the field, or among different fields, as indicated by block 436. The damage consequence metric can be generated during subsequent operations (such as operations later in the season, during subsequent years in the field, or otherwise), as indicated by block 438. The damage consequence metric can be any of a wide variety of other damage consequence metrics obtained in other ways as well, as indicated by block 440.

Soil damage score output system 178 then also generates an output indicative of a consequence of inflicting the soil damage on the field, as indicated by block 442. Again, the consequence can be the affect on yield as indicated by block 444, or any of a wide variety of other outputs. The output indicative of a consequence of inflicting the soil damage can be stored in data store 142 or another data store, as indicated by block 446. The consequence can be communicated to other systems as well, as indicated by block 448. The output indicative of a consequence of inflicting soil damage can be generated in other ways, and be output in other ways as well, as indicated by block 450.

As discussed above, there are a wide variety of different types of agricultural vehicles that have a load that varies during operation of the vehicle within a field. Excessive soil compaction can damage the field, and therefore, agricultural vehicles that are carrying a heavy load can compact the field in undesirable ways. Many such machines have inflatable tires. Also, some such machines have tire inflation systems which automatically adjust the inflation pressure in the tires of the machine, based on an input, such as from a load cell mounted in the axle of the vehicle or from an operator.

It can be desirable to adjust the tire inflation pressure during operation of the agricultural machine. For instance, when the machine is traveling over a road, the tire inflation pressure may be increased to a rated maximum pressure in order to increase fuel efficiency. However, once the agricultural machine enters the field, it may be desirable to reduce the inflation pressure in order to increase an area of a contact patch between the tire and the field in order to spread the load carried by the tire over a larger area, to thus mitigate undesirable compaction which may result from the vehicle traveling over the field.

Some current systems, as briefly mentioned above, use load cells mounted in the axle of the vehicle in order to detect the load being carried by the vehicle. The detected load can be used to automatically adjust the inflation pressure in the tires. However, this is a relatively complex system and can be difficult to retrofit into an already-existing vehicle.

The present discussion thus proceeds with respect to a system that automatically detects the fill level of material in the agricultural vehicle and adjusts the inflation pressure in the tires based upon the detected fill level. The fill level can be used to determine a load that may be carried by the vehicle, and the load can then be used to adjust the inflation pressure. Similarly, the fill level can be used to control the inflation pressure for all tires or for different subsets of the tires or for individual tires. For example, the fill level and material distribution can be detected and used to identify the overall load carried by the vehicle, the load on a per-axle basis, or the load on a per-tire basis, and the load can be used to adjust the inflation pressure of all tires, of tires on a per-axle basis, or of individual tires on a per-tire basis.

Figure 7:
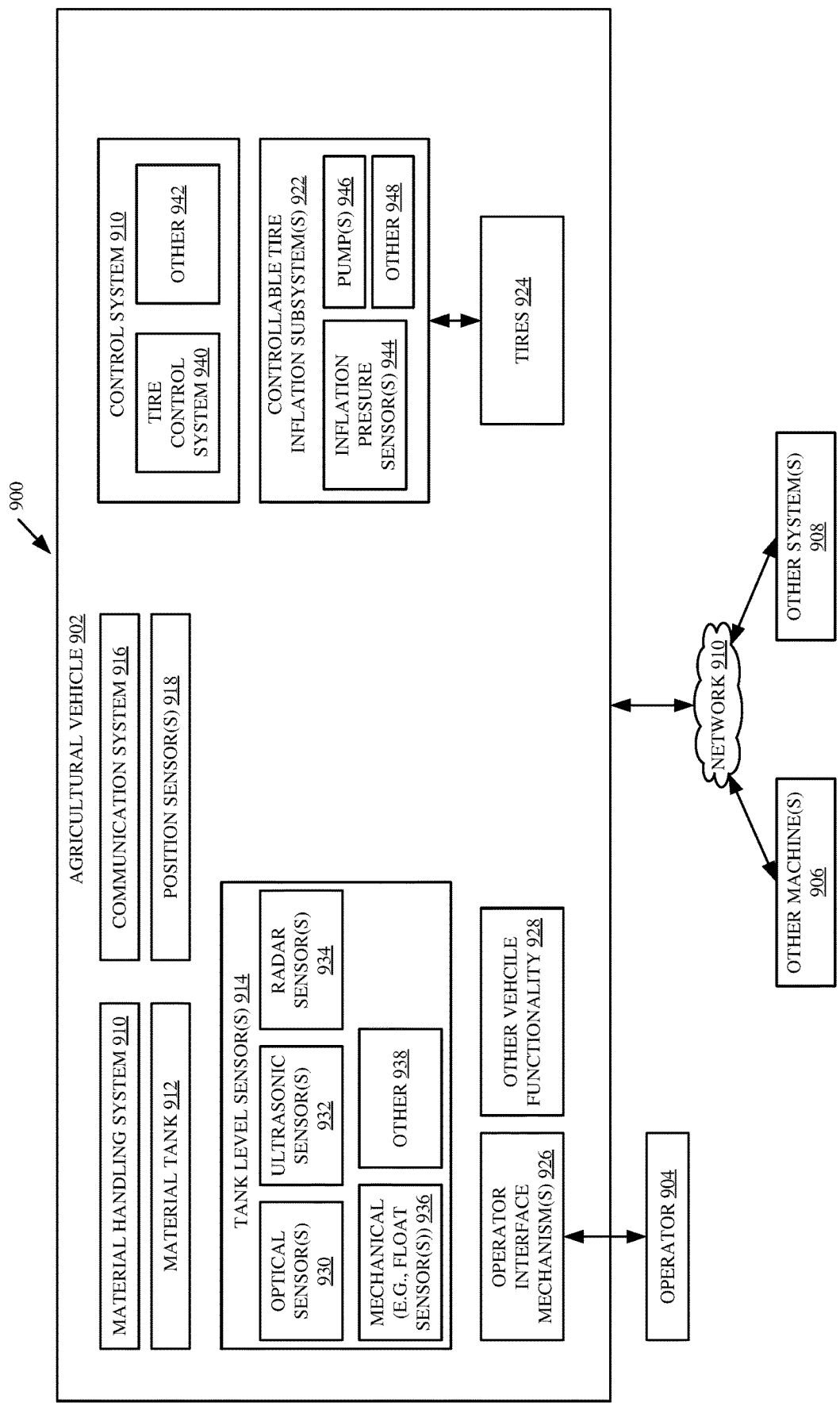
FIG. 7 is a block diagram of one example of an agricultural system.

FIG. 7 is a block diagram of one example of an agricultural system 900 which may be similar to, or different from, agricultural system 100. FIG. 7 shows an example of an agricultural system 900 in which agricultural vehicle 902 may be operated by an operator 904 (who may be local to or remote from, vehicle 902) or vehicle 902 may be autonomously operated. System 900 also shows that, in one example, agricultural vehicle 902 can communicate with other machines 906 and/or other systems 908 over a network 910. Network 910 can thus be a wide area network, a local area network, a near field communication network, a cellular communication network, or any of a wide variety of other networks or combinations of networks. Other machines 906 may be other machines operating in the same field or vicinity as vehicle 902 or machines located elsewhere. Other systems 908 may be cloud-based systems, farm manager systems, vender systems, manufacturer systems, or other systems that may be remote from vehicle 902.

In the example shown in FIG. 7, agricultural vehicle 902 includes material handling system 910, material tank 912, tank level sensor(s) 914, communication system 916, position sensors 918, control system 920, controllable tire inflation subsystem 922, tires 924, operator interface mechanisms 926, and other vehicle functionality 928. Tank level sensor(s) 914 can include one or more of optical sensor(s) 930, ultrasonic sensor(s) 932, radar sensor(s) 934, mechanical sensor(s) (such as float or deflectable finger sensor(s)) 936, or other sensor(s) 938. Control system 920 can include tire control system 940 and other control system functionality 942. Controllable tire inflation subsystem 922 can include inflation pressure sensor(s) 944, one or more pumps 946, and other tire inflation subsystem functionality 948. Before describing the operation of the overall architecture 900 in more detail, a description of some of the items in agricultural vehicle 902, and their operation, will first be described.

Material handling system 910 may have different functionality and mechanisms, depending on the type of agricultural vehicle 902. For instance, where vehicle 902 is a harvester, material handling system 910 will have harvesting mechanisms and functionality to harvest material and move the material to material tank 912. Where agricultural vehicle 902 is an application vehicle which applies material to the field, then that material (such as fertilizer, insecticide, pesticide, or other commodity) may be stored in material tank 912 and dispensed onto the field through material handling system 910, in which case material handling system 910 may be a pump with sprayers and nozzles, or other application mechanisms and functionality that take material from tank 912 and apply it to the field. Where agricultural vehicle 902 is a planter, then material handling system 910 may include mechanisms that move seed from an air cart (e.g., tank 912), for example, to a row unit for placement in the ground. Where vehicle 902 is a grain cart, material handling system 910 may be an auger or lower hatch or other unloading system that can be used to unload the material from tank 912 on a grain cart into another vehicle or at another unloading location.

Tank level sensors 914 sense the level of material in tank 912. Optical sensors 930, for instance, can include a camera which captures an image (either a still image or a video image) along with image processing functionality that identifies the surface of the material in tank 912 so that the level of material in tank 912 can be identified. Ultrasonic sensor(s) 932 can be mounted relative to tank 912 to ultrasonically identify the fill level of material in tank 912. Similarly, radar sensor(s) 934 can be mounted relative to tank 912 to identify the fill level of material in tank 912 using radar. Mechanical sensor(s) 936 can be configured to mechanically sense the fill level of material in tank 912. For instance, where the material is liquid, mechanical sensor(s) 936 may include one or more floats that are used to detect the fill level of material in tank 912. Where the material is granular or a different type of material, mechanical sensor(s) 936 may be deflectable fingers, or other mechanical sensors that sense a signal indicative of the fill level of material in tank 912.

Communication system 916 facilitates the communication among the items on vehicle 902, and also with other machines 906 and other systems 908 over network 910. Therefore, communication system 916 can include a controller area network (CAN) bus and bus controller, and system 916 may vary based upon the type of network 910 over which it is communicating and based upon the type of network on vehicle 902 over which it is communicating.

Position sensors 918 can be mounted on agricultural vehicle 902 and generate a position sensor signal indicative of a geographic location or position (e.g., location and/or heading) of vehicle 902. Therefore, position sensor 918 can be a global navigation satellite system (GNSS) receiver, a dead reckoning system, a cellular triangular system, or any of a wide variety of other sensors. In one example, position sensor 918 can generate signals indicative of the speed of travel of vehicle 902 and other information as well.

Operator interface mechanisms 926 can include any of a wide variety of different types of mechanisms that can be used to interface with operator 904. Operator interface mechanisms 926 can thus be a steering wheel, a joystick, buttons, switches, levers, linkages, knobs, etc. In addition, operator interface mechanisms 926 can include a display screen with user actuatable elements, such as icons, links, actuatable buttons, or other actuatable items that are displayed on the display screen and that can be actuated using a touch gesture (where the screen is a touch sensitive display screen), a point and click device, voice commands, etc. Operator interface mechanisms 926 can also include a microphone and speaker (such as where speech recognition and/or speech synthesis functionality is provided), or any of a wide variety of audio, visual, and/or haptic mechanisms that can be used to convey information to operator 904 and to receive information and from operator 904. Operator interface mechanisms 926 illustratively generate output signals indicative of received operator inputs and provide those signals to other items on agricultural vehicle 902.

Control system 920 can include processors and/or servers, as well as associated memory and timing circuitry, that can be used to receive inputs (such as from sensors, operator inputs, other items on vehicle 902 or located elsewhere, etc.) and generate outputs to control different functionality on vehicle 902 based on those inputs.

Tire control system 940 illustratively receives inputs, such as from tire level sensor(s) 914, position sensor(s) 918, operator interface mechanism(s) 926 and/or other items on vehicle 902, identifies a target inflation pressure for tires 924, and generates control signals that are provided to controllable tire inflation subsystem 922 in order to control the inflation pressure in tires 924. In one example, tire control system 940 receives a tank level sensor signal from one of sensors 914 and calculates the load on tires 924, based upon the level of material in material tank 912. Given the load on tires 924, or given the fill level itself, tire control system 940 identifies the target inflation pressure(s) and generates control signals that are provided to controllable tire inflation subsystem 922 in order to control the inflation pressure in tires 924. In one example, the inflation pressure sensor(s) 944 sense the inflation pressure in tires 924 and provide a pressure signal to tire control system 940 indicative of the inflation pressure in the tires 924. Based on that pressure, and the desired target pressure for tires 924, tire control system 940 generates a control signal to control one or more pumps 946 to control the tire inflation pressure in tires 924.

In another example, tire control system 940 may receive an input from position sensor 918 indicating the geographic location and heading of vehicle 902. Tire control system 940 can then determine whether vehicle 902 is in a field or on a road, based upon its geographic location, by accessing a map. If vehicle 902 is on a road, then tire control system 940 can generate a control signal to control the controllable tire inflation system 922 so that tires 924 are inflated to their maximum rated inflation pressure. However, if vehicle 902 is in a field, then tire control system 940 can identify the load on the tires 924 and control the inflation pressure to maximize the contact patch between tires 924 and the field over which it is traveling, based on the level of material in tank 912, based the load on the tires, and/or based on any other desired inputs.

Figure 8:
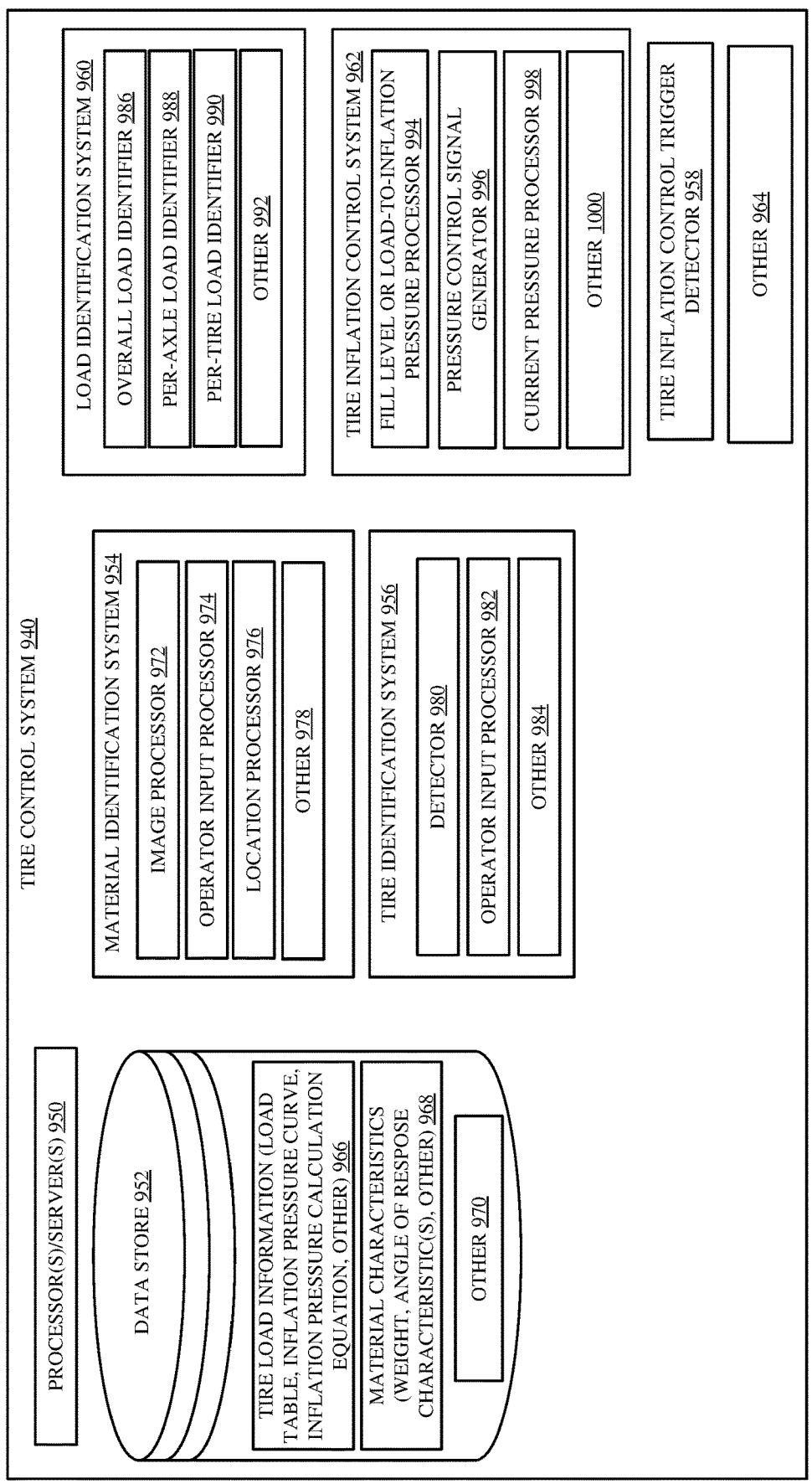
FIG. 8 is a block diagram showing one example of a tire control system.

FIG. 8 is a block diagram showing one example of tire control system 940, in more detail. In the example shown in FIG. 8, tire control system 940 includes one or more processors or servers 950, data store 952, material identification system 954, tire identification system 956, tire inflation control trigger detector 958, load identification system 960, tire inflation control system 962, and other items 964. Data store 952 can, itself, include tire load information 966, which may be in the form of a load table (or set of load tables), an inflation pressure curve (or set of curves), inflation pressure calculation equation (or set of equations), or other information that can be used by load identification system 960 to calculate the load on the tires 924 based upon the level of material in tank 912. Data store 952 can also include material characteristics 968 which may be indicative of the weight of the material, the angle of repose of the material in the tank 912, or other characteristics. By way of example, different types of kernels (corn, soybeans, oats, etc.) may physically interact with one another differently, when they are in a pile. Therefore, the angle of the surface of the pile in which those kernels reside in a tank that is being filled with an auger, for instance, may be different and may thus affect the load distribution in the tank 912. Characteristics indicative of how the kernels interact with one another may, for instance, be stored as characteristics 968 and be considered when identifying the load on the tires 924. Material characteristics 968 can include other characteristics as well. Similarly, data store 952 can include a wide variety of other information 970.

Material identification system 954 can be used to identify the type of the material in material tank 912. Material identification system 954 can include an image processor 972 that generates an image of the material in tank 912 and processes that image to identify the type of material (such as corn, soybeans, fertilizer, etc.) in tank 912. Material identification system 954 can also include operator input processor 974 which receives an operator input indicative of the type of material in tank 924. Similarly, material identification system 954 can include location processor 976. When vehicle 902 is a harvester, for example, location processor 976 can receive a location signal from position sensor 918 and access a data store or other information indicating what type of crop was planted at that location and can thus identify the type of material in tank 912 based upon the location of the vehicle. Material identification system 954 can include any of a wide variety of other items 978 that can be used to identify the type of material in tank 912.

Tire identification system 956 can detect the type (e.g., make, model, and/or other information) of tires 924, and thus access information to identify the rated inflation pressure for those tires, and/or other physical or load characteristics or other characteristics of the tires 924. Tire identification system 956 can thus include a detector 980 that detects the type of tire. For instance, the tire may be encoded with an identifier (such as an RFID tag, or other written, stamped, magnetic, electric or other tire identifying information) which can be detected by detector 980. Operator input processor 982 can detect an operator input identifying the type of tire, and tire identification system 956 can also include other items 984 that detect the type of tire 924 in other ways (such as by identifying the type of vehicle 902 and using default tires for that type of vehicle, etc.).

Tire inflation control trigger detector 958 detects whether tire control system 940 should determine whether the inflation pressure in tires 924 needs to be adjusted. By way of example, tire inflation control detector 958 may receive an input from position sensor 918 that can be tracked to indicate the change in position of vehicle 902. Depending on the type of vehicle 902, it may be that the tire inflation pressure should be adjusted every 900 meters of travel of vehicle 902, or some other distance of travel. Therefore, tire inflation control trigger detector 958 can detect the distance that vehicle 902 has traveled to determine whether the tire inflation pressure should be adjusted. In another example, tire inflation control trigger detector 958 can detect when vehicle 902 moves from the road into a field or vice versa, and that may be a trigger indicating that the tire inflation pressure should be adjusted. Similarly, tire inflation control trigger detector 958 may receive an output from tank level sensor(s) 914 and/or from load identification system 960 indicating the fill level in tank 912 and/or the load on tires 924. When the fill level and/or load has changed sufficiently (such as by a threshold amount or another amount), then that may be a trigger that is detected by tire inflation control trigger detector 958 indicating that the tire inflation pressure should be adjusted. Trigger detector 958 can detect other triggers that indicate that the tire inflation pressure should be adjusted as well.

Load identification system 960 illustratively includes overall load identifier 986, per-axle load identifier 988, per-tire load identifier 990 and it can include other items 992. Load identification system 960 identifies the load on tires 924. Overall load identifier 986 can identify the overall load on the group of tires 924 on vehicle 902. Per-axle load identifier 988 can identify the load on the tires on each axle of vehicle 902, and per-tire load identifier 990 can identify the load on each of the individual tires 924 on vehicle 902. In one example, load identification system 960 receives the tank level sensor signal from sensor(s) 914 indicative of the level of material in tank 912 from one or more of sensors 914 and identifies the load on the tires 924 based upon the material level in tank 912. In another example, load identification system 960 not only receives the material level from one or more of sensors 914 but also receives the material type from material identification system 954. Based upon the material type and the fill level, load identification system 960 can access the material characteristics 968 to calculate the load on the tires 924. Again, the load can be an overall load, a per-axle load, a per-tire load, and/or another load indicator that indicates the load on tires 924.

Tire inflation control system 962 illustratively includes fill level or load-to-inflation pressure processor 994, pressure control signal generator 996, current pressure processor 998, and other items 1000. Tire inflation control system 962 can identify the target inflation pressure for tires 924 either directly from the fill level in tank 912 or based on the load output by load identification system 960. Tire inflation control system 962 is described as identifying the target inflation pressure for tires 924 based on the load, but this is for the sake of example only and the target inflation pressure can be identified just from the fill level. For example, the target inflation pressure can be determined directly from the fill level using a lookup table or using a linear conversion function or another equation or another method. The minimum and maximum rated tire pressures can be determined, based on an operator input or by using default values, and then scaled based on fill level, for instance.

Continuing with the example, tire inflation control system 962 receives the load signal from load identification system 960, indicating the load on the tires 924 and identifies a target inflation pressure for the tires 924, based upon the load. In one example, fill level or load-to-inflation pressure processor 994 receives the load signal from load identification system 960 and accesses tire load information 966 to identify the target pressure for the tires 924, based upon the load. In identifying the target inflation pressure, processor 994 may also receive an input from tire identification system 956 identifying the type of tire 924 so that the maximum and/or minimum rated inflation pressures can be identified as well as other information.

Fill level or Load-to-inflation pressure processor 994 may access tire load information 166 that is stored in the form of a load table which identifies a tire inflation pressure value, for a particular type of tire (or for a default type of tire) based upon the load on that tire. There may be different tables for different types of tires, conditions, etc. Processor 994 may access an inflation pressure curve which is a curve that identifies the target inflation pressure for a tire 924 based upon the load. There may be different curves for different types of tires or different operating conditions, etc. Processor 994 may use an inflation pressure calculation equation which can be used to calculate the target inflation pressure, given the load, for tires 924. Again, there may be different equations for different types of tires, for different types of vehicle 902, for different operating conditions, etc.

Once the fill level or load-to-inflation pressure processor 994 identifies the target inflation pressure for tires 924, current pressure processor 998 receives a signal from inflation pressure sensor 944 (in FIG. 7) that identifies the inflation pressure in tires 924. The inflation pressure can be sensed in each of the tires 924, in a representative subset of the tires 924, or in other ways. Pressure control signal generator 996 compares the current inflation pressure in tires 924 to the target pressure generated by load-to-inflation pressure processor 994 to determine whether an inflation pressure adjustment needs to be made. If so, pressure control signal generator 996 generates control signals and provides the control signals to controllable tire inflation subsystem 922 to control the inflation pressure in tires 924. For example, the control signals may control pumps 946 to increase or decrease the inflation pressure in tires 924.

Figure 9A:
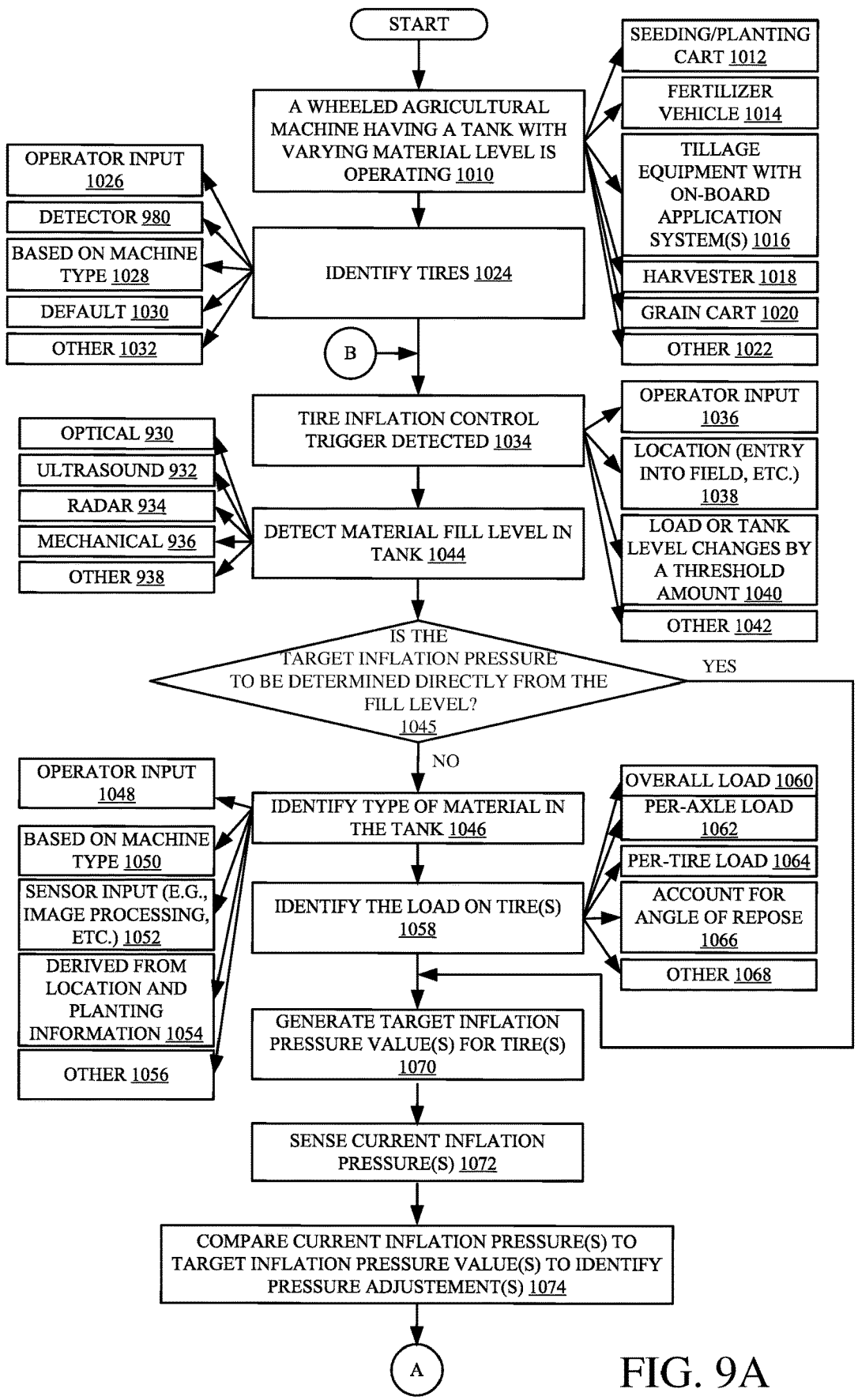
FIGS. 9A and 9B (collectively referred to herein as FIG. 9) show a flow diagram illustrating one example of the operation of the agricultural system.
Figure 9B:
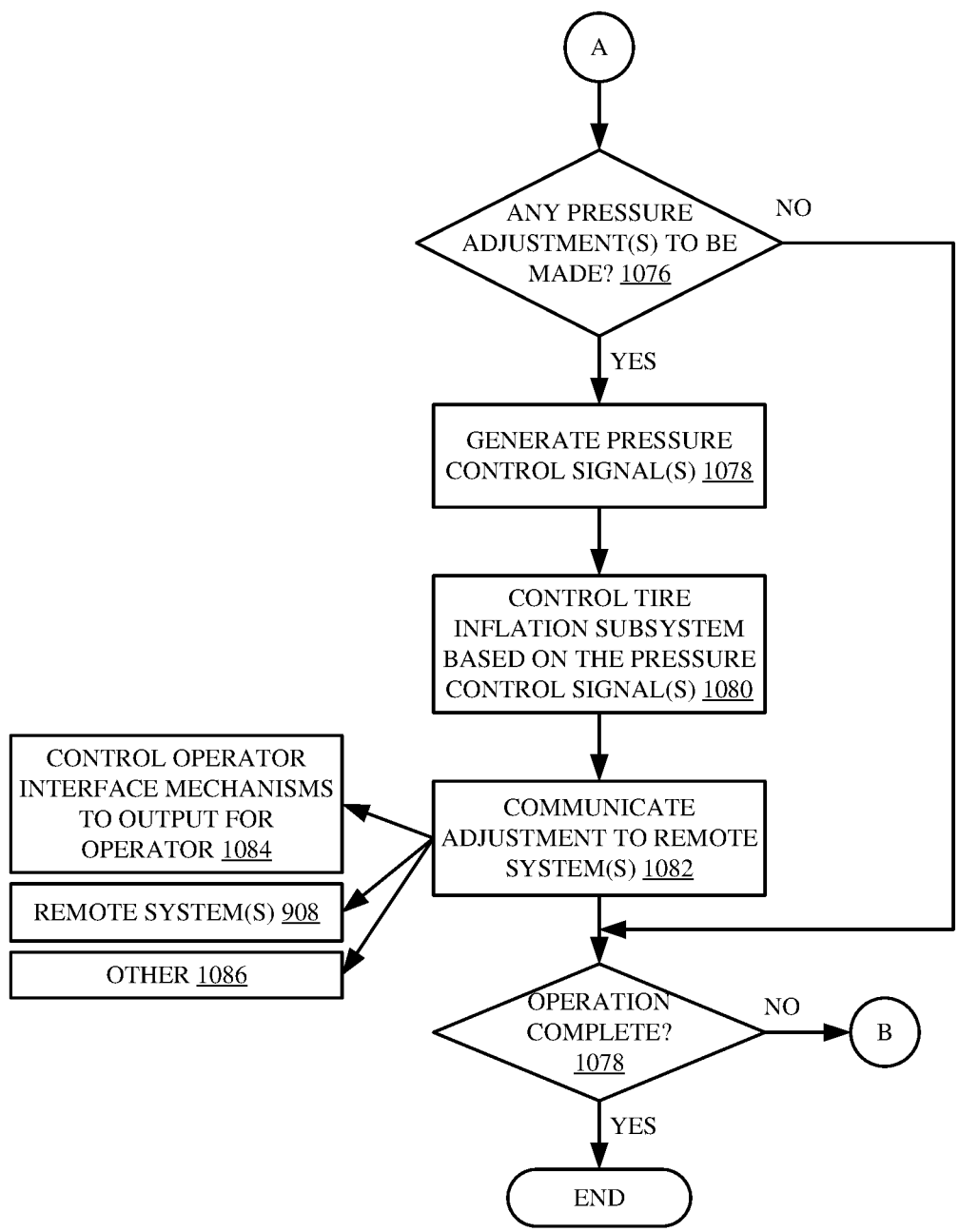

FIGS. 9A and 9B (collectively referred to herein as FIG. 9) show a flow diagram illustrating one example of the operation of agricultural system 900 in detecting a material level in material tank 912 and controlling tire inflation pressure in tires 924 based upon that material level. It is first assumed that a wheeled agricultural machine that has a material tank 912 with a varying material level is operating, as indicated by block 1010. The agricultural machine can be a seeding machine or planting/seed cart 912, a fertilizer vehicle 1014, tillage equipment with on-board application system 1016, a harvester 1018, a grain cart 1020, or other items 1022. Some additional examples of machines or vehicles 902 are described below with respect to FIGS. 10-14.

Where tire identification system 956 is provided, then tire identification system 956 identifies the type of tires 924 that are on the machine or vehicle 902. Identifying the tires is indicated by block 1024. Operator input processor 982 can detect the type of tires based upon an operator input 1026. The type of tires can be automatically detected by detector 980. The type of tires can be inferred based upon the type of agricultural vehicle 902, as indicated by block 1028. The type of tire may be a default tire 1030, or the type of tire may be determined in other ways as well, as indicated by block 1032.

Tire inflation control trigger detector 958 detects a tire inflation control trigger, as indicated by block 1034. The tire inflation control trigger may be detected based upon an operator input 1036, based upon the location of vehicle 902 as indicated by position sensor 918 and as indicated by block 1038 in the flow diagram of FIG. 9, based on load or fill level changes, as indicated by block 1040, or in other ways, as indicated by block 1042.

Tank level sensors 914 generate an output indicative of the level of material in tank 912. Detecting the material fill level in the tank is indicated by block 1044 in the flow diagram of FIG. 9. As discussed above, tank level sensor(s) 914 can be optical sensor(s) 930, ultrasonic sensor(s) 932, radar sensor(s) 934, mechanical sensor(s) 936, or other sensor(s) 938. If the target inflation pressure is to be determined directly from the fill level then processing may skip to block 1070, as indicated by block 1045 and as discussed elsewhere. However, if the target inflation pressure is determined based on the load, then processing continues at block 1046.

Where material identification system 954 is used, then system 954 identifies the type of material in the tank 912, as indicated by block 1046 in the flow diagram of FIG. 9. Again, the type of material may be identified using an operator input 1048, based upon the type of machine or vehicle 902 as indicated by block 1050, based upon a sensor input, such as from an image processor, as indicated by block 1052, based upon location information derived from a current location of vehicle 902 as well as planting information indicating the type of crop in that field, as indicated by block 1054. The type of material can be identified in a wide variety of other ways as well, as indicated by block 1056.

Where load identification system 960 is used, load identification system 960 then identifies the load on the tires 924, as indicated by block 1058 in the flow diagram of FIG. 9. The load can be the overall load 1060, the per-axle load 1062, or the per-tire load 1064. Also, the load on each of the tires 924 (or subsets of the tires 924) can account for the angle of repose of the material in tank 912. For instance, if the material is being loaded into tank 912 at one end of tank 912 the characteristics 968 may indicate that the material may tend to pile up at that end of tank 912 without distributing evenly across tank 912. In that case, the angle of repose would indicate that the load on some subset of tires may be higher than the load on another subset of tires. Accounting for the angle of repose of material in tank 912 is indicated by block 1066. The load can be identified in other ways as well, as indicated by block 1068.

Tire inflation control system 962 then generates a target inflation pressure value for the tires 924, as indicated by block 1070. In one example, fill level or load-to-inflation pressure processor 994 identifies the target inflation pressure directly from the sensed fill level. In another example, processor 994 identifies the target inflation pressure based on the load. Fill level or load-to-inflation pressure processor 994 can identify the target inflation pressure in a variety of other ways as well, some of which were discussed elsewhere.

Current pressure processor 998 then senses, or receives a signal indicative of, the current inflation pressure in the tires 924, as indicated by block 1072. Pressure control signal generator 196 then compares the current inflation pressure in tires 924 to the target inflation pressure values to identify whether any pressure adjustments are needed, and if so, the value of those adjustments, as indicated by block 1074.

If, at block 1076, it is determined that no adjustments are needed, then operation continues at block 1078. Until the operation being performed by vehicle 902 is complete, operation reverts to block 1044 where the tire inflation control trigger detects additional tire inflation control triggers at block 1034.

However, if, at block 1076, it is determined that a tire inflation pressure adjustment is to be made, then pressure control signal generator 996 generates pressure control signals and provides the pressure control signals to controllable tire inflation subsystem 922, as indicated by block 1078. The control signals control the pump 946 or other items in controllable tire inflation subsystem 922 to inflate or deflate tires 924 to the target inflation pressure, as indicated by block 1080.

In one example, communication system 916 can then communicate the adjustments to other machines 906 or other remote systems 908, as indicated by block 1082. Similarly, communication system 916 can control operator interface mechanisms 926 to provide an indication of the pressure adjustments to operator 904, as indicated by block 1084. For example, the operator interface mechanisms 926 may include a display that shows a representation of each of the tires 924 on vehicle 902, their current inflation pressure, current loads, and the target inflation pressure. The display may be updated to show that the current inflation pressure is being changed or adjusted to the target inflation pressure as well. Communication system 916 may also output the adjustment values to other systems 908, or in other ways, as indicated by block 1086 in the flow diagram of FIG. 9.

It can thus be seen that the present description describes a system which senses the material fill level in a material tank on an agricultural vehicle. Based on the material fill level, the inflation pressure in the tires of the agricultural vehicle 902 are controlled. In one example, the inflation pressure can be controlled to maximize the contact patch between the tire and the field over which it is traveling, given the load on the tire.

Figure 10:
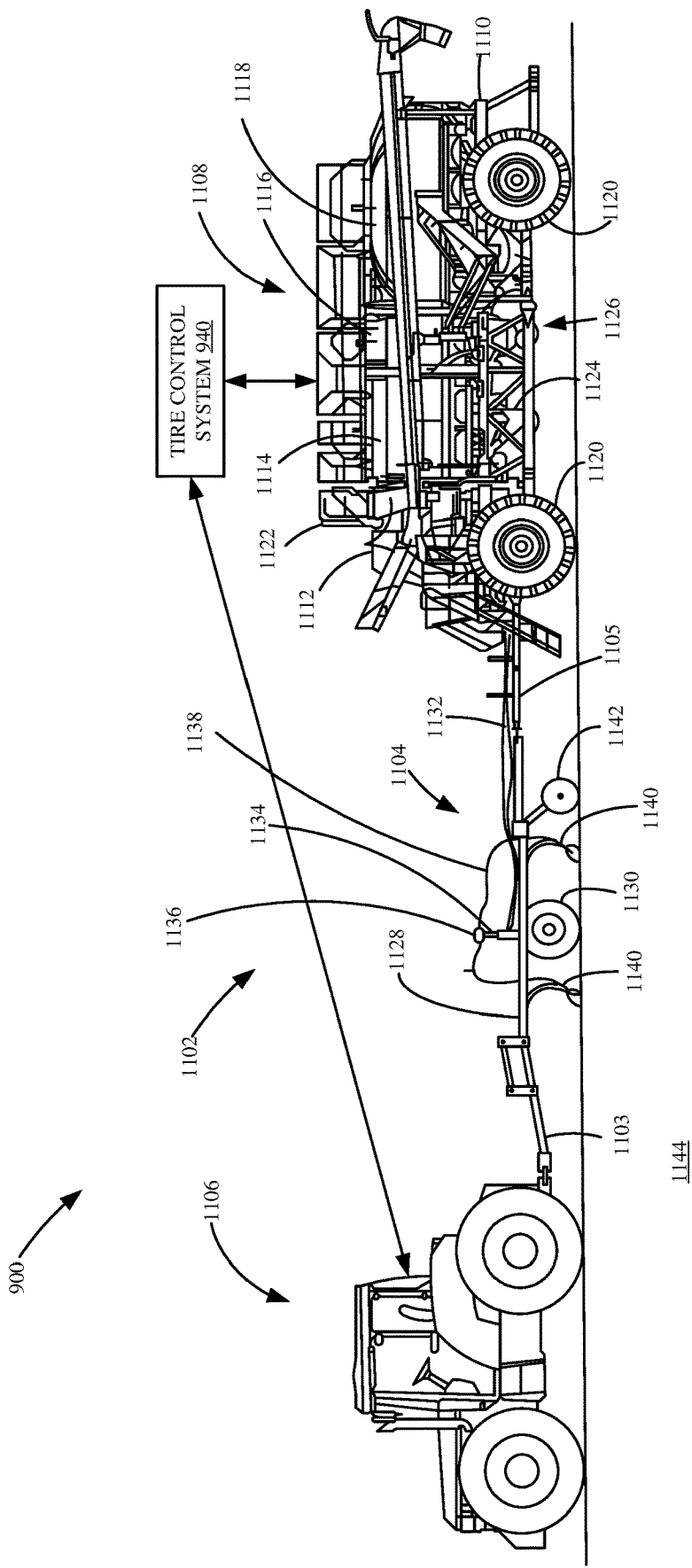
FIG. 10 is a partial pictorial, partial block diagram of a planter.

FIG. 10 is a side view of an example of a portion of an agricultural system 900 in which the agricultural vehicle 902 includes an agricultural implement, in particular an air or pneumatic seeder 1102. In the example shown in FIG. 10, the seeder 1102 comprises a tilling implement (or seeding tool) 1104 (also sometimes called a drill) towed between a tractor (or other towing vehicle) 1106 and a commodity cart (also sometimes called an air cart) 1108. The commodity cart 1108 has a frame 1110 upon which a series of product tanks 1112, 1114, 1116, and 1118, and wheels 1120 are mounted. Each product tank has a door (a representative door 1122 is labeled) releasably sealing an opening at its upper end for filling the tank with product, most usually a commodity of one type or another. A metering system 1124 is provided at a lower end of each tank (a representative one of which is labeled) for controlled feeding or draining of product (most typically granular material) into a pneumatic distribution system 1126. The tanks 1112, 1114, 1116, and 1118 can hold, for example, a material or commodity such as seed or fertilizer to be distributed to the soil. The tanks can be hoppers, bins, boxes, containers, etc. The term "tank" shall be broadly construed herein. Furthermore, one tank with multiple compartments can also be provided instead of separated tanks.

The tilling implement or seeding tool 1104 includes a frame 1128 supported by ground wheels 1130. Frame 1128 is connected to a leading portion of the commodity cart 1108, for example by a tongue style attachment (not labeled). The commodity cart 1108 as shown is sometimes called a "tow behind cart," meaning that the cart 1108 follows the tilling implement 304. In an alternative arrangement, the cart 1108 can be configured as a "tow between cart," meaning the cart 1108 is between the tractor 1106 and tilling implement 1104. In yet a further possible arrangement, the commodity cart 1108 and tilling implement 1104 can be combined to form a unified rather than separated configuration. These are just examples of additional possible configurations. Other configurations are even possible and all configurations should be considered contemplated and within the scope of the present description.

In the example shown in FIG. 10, tractor 1106 is coupled by couplings 1103 to seeding tool 1104 which is coupled by couplings 1105 to commodity cart 1108. The couplings 1103 and 1105 can be mechanical, hydraulic, pneumatic, and electrical couplings and/or other couplings. The couplings 1103 and 1105 can include wired and wireless couplings as well.

The pneumatic distribution system 1126 includes a fan (not shown) connected to a product delivery conduit structure having multiple product flow passages 1132. The fan directs air through the flow passages 1132. Each product metering system 1124 controls delivery of product from its associated tank at a controllable rate to the transporting airstreams moving through flow passages 1132. In this manner, each flow passage 1132 carries product from the tanks to a secondary distribution tower 1134 on the tilling implement 1104. Typically, there will be one tower 1134 for each flow passage 1132. Each tower 1134 includes a secondary distributing manifold 1136, typically located at the top of a vertical tube. The distributing manifold 1136 divides the flow of product into a number of secondary distribution lines 1138. Each secondary distribution line 1138 delivers product to one of a plurality of ground engaging tools 1140 (also known as ground openers) that define the locations of work points on seeding tool 1104. The ground engaging tools 1140 open a furrow in the soil 1144 and facilitates deposit of the product therein. The number of flow passages 1132 that feed into secondary distribution may vary from one to eight or ten or more, depending at least upon the configuration of the commodity cart 1108 and tilling implement 1104. Depending upon the cart and implement, there may be two distribution manifolds 1136 in the air stream between the meters 1124 and the ground engaging tools 1140. Alternatively, in some configurations, the product is metered directly from the tank or tanks into secondary distribution lines that lead to the ground engaging tools 1140 without any need for an intermediate distribution manifold. The product metering system 1124 can be configured to vary the rate of delivery of seed to each work point on tool 1104 or to different sets or zones of work points on tool 1104. The configurations described herein are only examples. Other configurations are possible and should be considered contemplated and within the scope of the present description.

A firming or closing wheel 1142 associated with each ground engaging tool 1140 trails the tool and firms the soil over the product deposited in the soil. In practice, a variety of different types of tools 1140 are used including, but not necessarily limited to, tines, shanks and disks. The tools 1140 are typically moveable between a lowered position engaging the ground and a raised position riding above the ground. Each individual tool 1140 may be configured to be raised by a separate actuator. Alternatively, multiple tools 1140 may be mounted to a common component for movement together. In yet another alternative, the tools 1140 may be fixed to the frame 1128, the frame being configured to be raised and lowered with the tools 1140.

Examples of air or pneumatic seeder 1102 described above should not be considered limiting. The features described in the present description can be applied to any seeder configuration, or other material application machine, whether specifically described herein or not. Settings can be used to set pneumatic pressure, travel speed, down force, seeding rate, material application rate, among others.

FIG. 10 also shows that tire control system 940 (and controllable subsystem 922 shown in FIG. 7) can be located anywhere on vehicle 1102, such as on tractor 1106 or implement 1106, 1108. The load carried by commodity cart 1108 varies as machine 1102 plants. Also, the commodity in each of the different tanks 1112, 1114, 1116, and 1118 may vary at different rates so the load on wheels 1120 may vary differently. In one example, tire control system 940 senses the fill level in each tank 1112, 1114, 1116, and 1118 and calculates the load on the wheels 1120 (collectively or in subsets) based on the fill levels in the tanks, based on the types of materials in the tanks, and/or based on other criteria.

Figure 11:
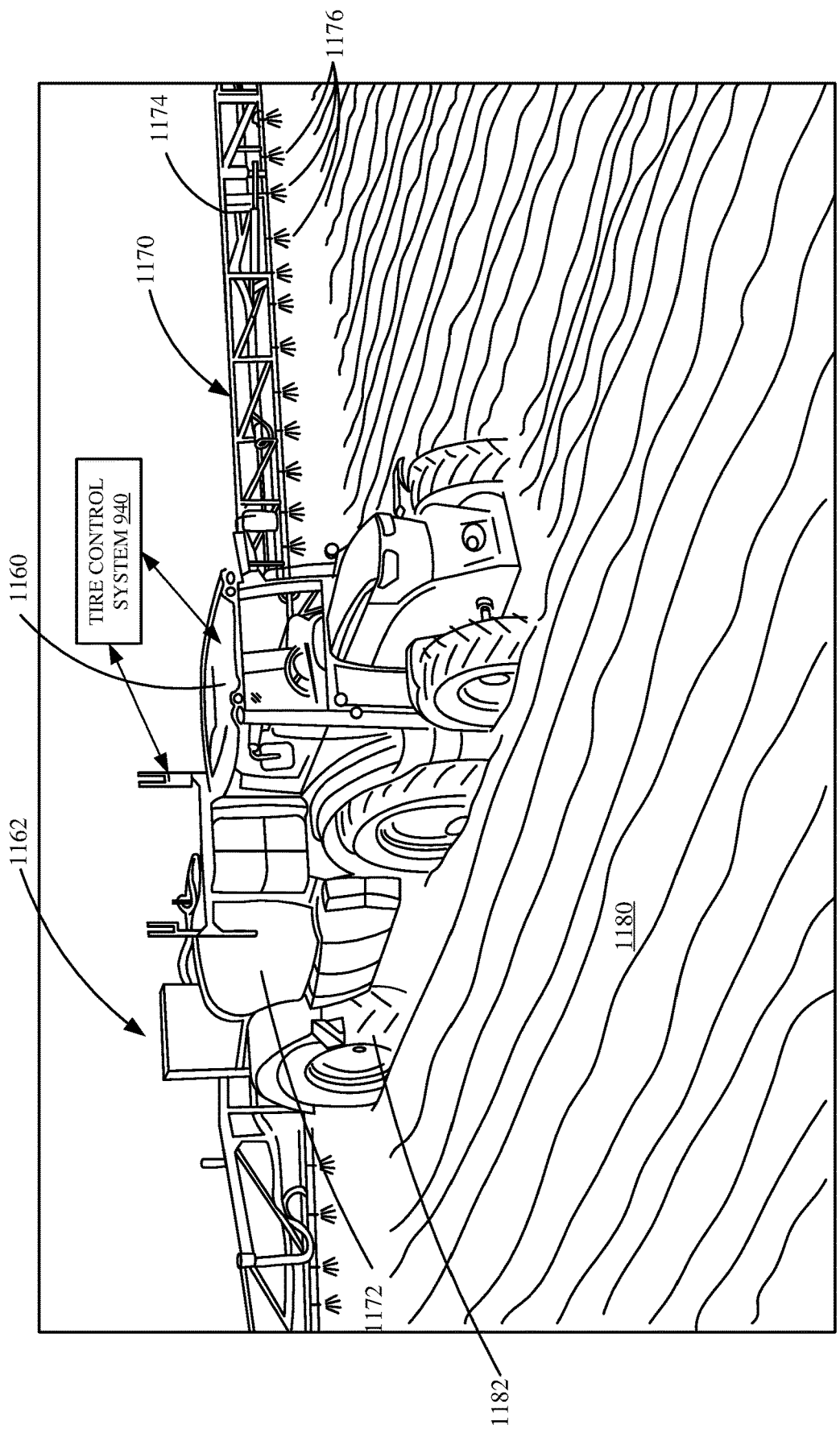
FIG. 11 is a partial pictorial, partial block diagram of a towed sprayer.

FIG. 11 illustrates an example of a portion of agricultural system 900 in which the agricultural vehicle 902 includes a tractor 1160 that is coupled to, and pulls, a towed sprayer 1162. Towed sprayer 1162 includes spray system 1170, which has a tank 1172 containing a liquid that is being applied to field 1180. Tank 1172 is mounted on a frame carried by tires 1182. Tank 1172 is also coupled to boom 1174, and the product is delivered to spray nozzles 1176, which are spaced apart along boom 1174. In FIG. 11 tractor 1160 and/or sprayer 1162 can include a controllable tire inflation system 922 (shown in FIG. 7) and tire control system 940 can be carried by tractor 1160 or on towed sprayer 1162 (or distributed) so the inflation pressure in tires 1182 can be adjusted automatically during operation, as the fill level in tank 1172 varies.

Figure 12:
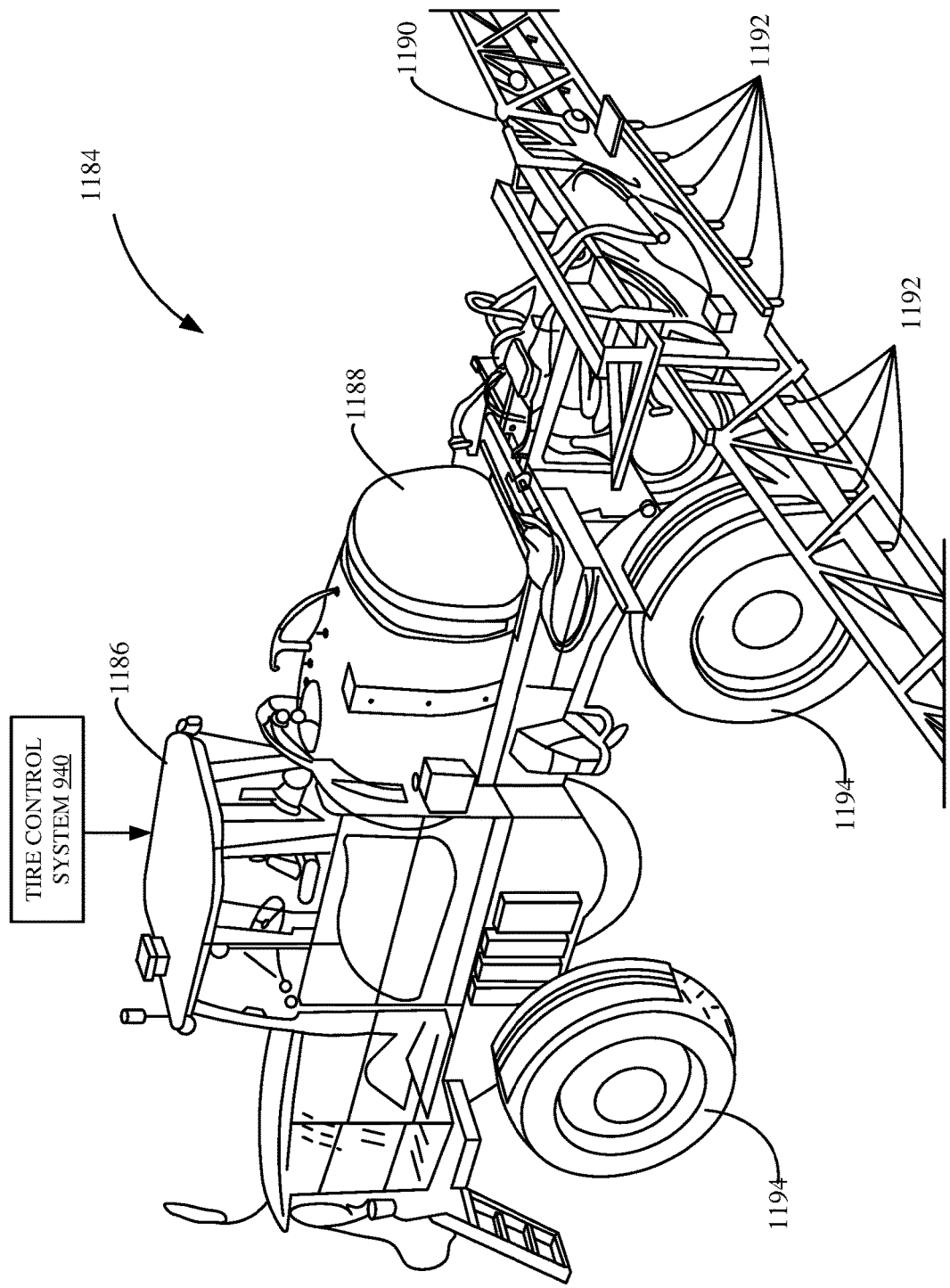
FIG. 12 is a partial pictorial, partial block diagram of a self-propelled sprayer.

FIG. 12 illustrates an example of a portion of architecture 900 in which the agricultural vehicle 902 includes a self-propelled agricultural sprayer 1184 that has an operator compartment 1186, tank 1188 (which carries material to be applied to the field), boom 1190, and a set of nozzles 1192. Sprayer 1184 can include tire control system 940 as well as a controllable tire inflation subsystem 922 (shown in FIG. 7). A pumping system pumps material from tank 1188 through nozzles 1192 to apply the material to the field. Tire control system 940 can automatically adjust the inflation pressure in tires 1194 (individually or in subsets) as the fill level of material in tank 1188 varies during operation of sprayer 1184.

Figure 13:
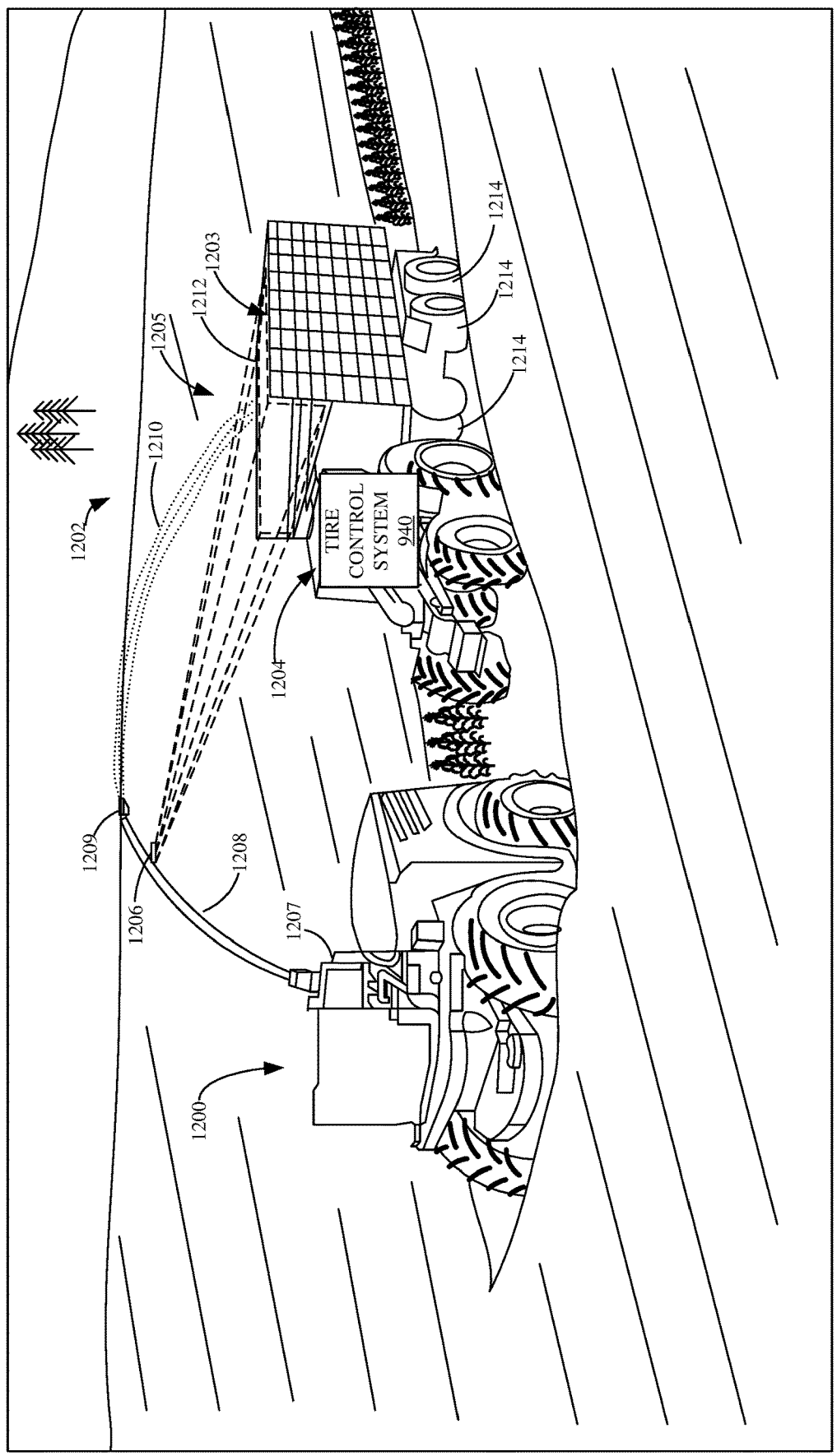
FIG. 13 is a partial pictorial, partial block diagram of a forage harvester unloading material into a receiving vehicle.

FIG. 13 is a pictorial illustration showing one example of a portion of architecture 900 in which agricultural vehicle 902 includes a receiving vehicle 1202 that is following a material loading vehicle, which is a self-propelled forage harvester 1200. Receiving vehicle 1202 includes tractor 1204 pulling grain cart 1205. Cart 1205 thus defines an interior that forms a receiving vessel 1203 for receiving harvested material through a receiving area 1212. In the example shown in FIG. 13, towing vehicle (e.g., a tractor) 1204, that is pulling grain cart 1205, is positioned directly behind forage harvester 1200 and has tire control system 1240 disposed thereon and receiving vehicle 1202 can include controllable tire inflation subsystem 1222 (shown in FIG. 7) as well. Also, in the example illustrated in FIG. 13, forage harvester 1200 has a camera 1206 mounted on the spout 1208 through which the harvested material 1210 is traveling. The spout 1208 can have a positionable flap 1209 and can be pivotally or rotationally mounted to a frame 1207 of harvester 1200. Camera 1206 can be a stereo-camera or a mono-camera that captures an image (e.g., a still image or video) of the receiving area 1212 of cart 1205. In the example shown in FIG. 13, the receiving area 1212 is defined by an upper edge of the walls of cart 1205.

When harvester 1200 has an automatic fill control system that includes image processing, the automatic fill control system can gauge the height of harvested material (the fill level) in cart 1205. The automatic fill control system can also generate a metric indicative of an overall or distributed fill level of cart 1205 based on the dimensions of cart 1205 and the sensed level of material in cart 1205. In one example, the fill level can be sent to tire control system 940 which can automatically adjust the inflation pressure in tires 1214 on cart 1205 (collectively or in subsets) based on the fill level in cart 1205. In another example, tank level sensor(s) 914 can be disposed on tractor 1204 or on cart 1205 to sense the fill level of material in cart 1205. Tire control system 940 can then automatically adjust the inflation pressure in tires 1214 based on the fill level.

By automatically, it is meant, for example, that the operation is performed without further human involvement except, perhaps, to initiate or authorize the operation.

Figure 14:
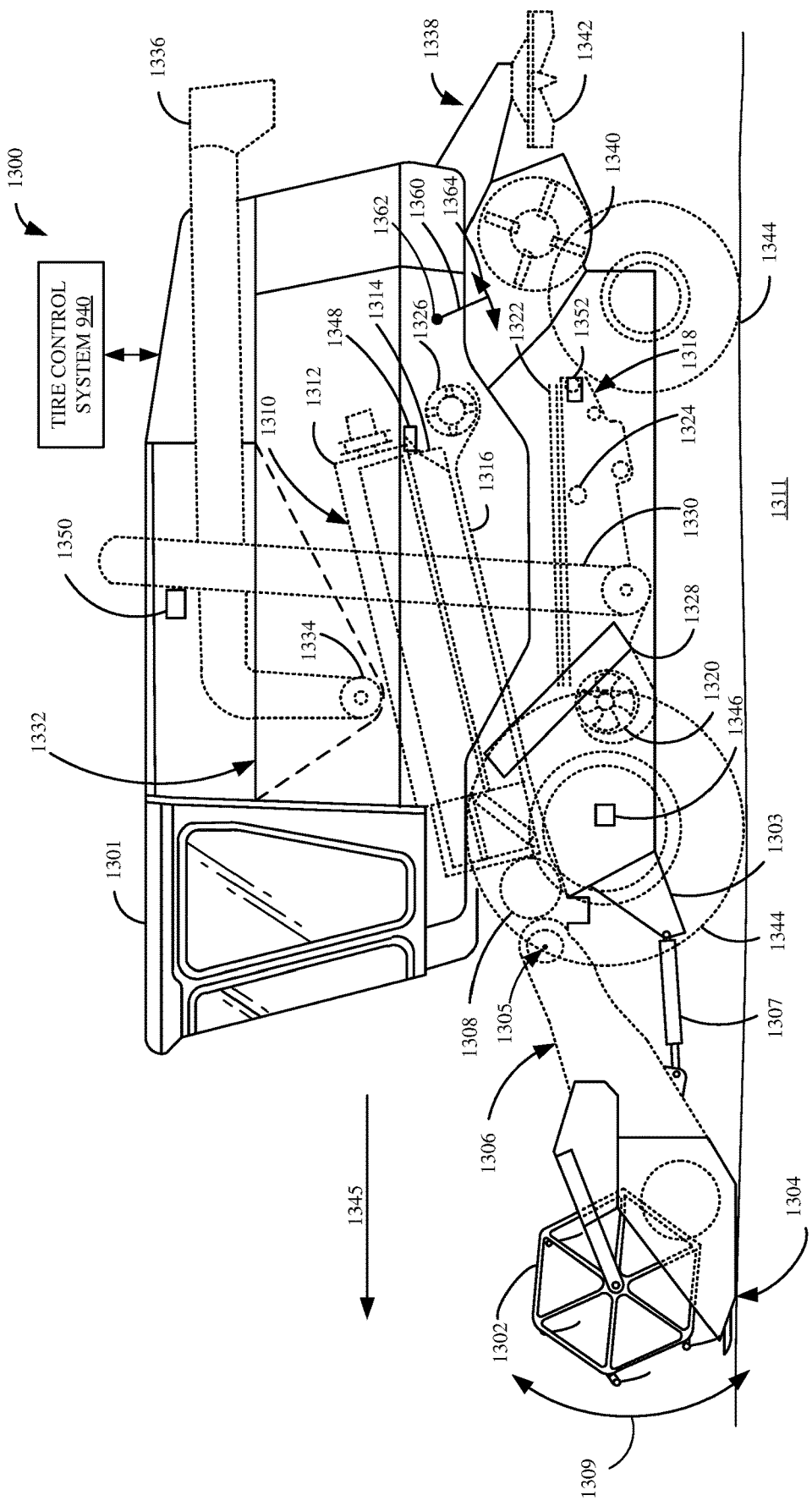
FIG. 14 is a partial pictorial, partial block diagram of a combine harvester.

FIG. 14 is a partial pictorial, partial schematic, illustration of one example of an agricultural system 900 in which agricultural vehicle 902 is a self-propelled agricultural harvesting machine 1300, in an example where machine 1300 is a combine harvester (or combine). It can be seen in FIG. 14 that combine 1300 illustratively includes an operator compartment 1301, which can have a variety of different operator interface mechanisms, for controlling combine 1300. Combine 1300 can include a set of front end equipment that can include header 1302, and a cutter generally indicated at 1304. It can also include a feeder house 1306, a feed accelerator 1308, and a thresher generally indicated at 1310. Header 1302 is pivotally coupled to a frame 1303 of combine 1300 along pivot axis 1305. One or more actuators 1307 drive movement of header 1302 about axis 1305 in the direction generally indicated by arrow 1309. Thus, the vertical position of header 1302 above ground 1311 over which it is traveling can be controlled by actuating actuator 1307. While not shown in FIG. 14 it may be that the tilt (or roll) angle of header 1302 or portions of header 1302 can be controlled by a separate actuator. Tilt, or roll, refers to the orientation of header 1302 about the front-to-back longitudinal axis of combine 1300.

Thresher 1310 illustratively includes a threshing rotor 1312 and a set of concaves 1314. Further, combine 1300 can include a separator 1316 that includes a separator rotor. Combine 1300 can include a cleaning subsystem (or cleaning shoe) 1318 that, itself, can include a cleaning fan 1320, chaffer 1322 and sieve 1324. The material handling subsystem in combine 1300 can include (in addition to a feeder house 1306 and feed accelerator 1308) discharge beater 1326, tailings elevator 1328, clean grain elevator 1330 (that moves clean grain into clean grain tank 1332) as well as unloading auger 1334 and spout 1336. Combine 1300 can further include a residue subsystem 1338 that can include chopper 1340 and spreader 1342. Combine 1300 can also have a propulsion subsystem that includes an engine that drives ground engaging wheels 1344. It will be noted that combine 1300 may also have more than one of any of the subsystems mentioned above (such as left and right cleaning shoes, separators, etc.). FIG. 14 shows that the combine 1300 also includes tire control subsystem 940, and combine 1300 can include a controllable tire inflation subsystem 922 as well (shown in FIG. 7).

In operation, and by way of overview, combine 1300 illustratively moves through a field in the direction indicated by arrow 1345. As it moves, header 1302 engages the crop to be harvested and gathers it toward cutter 1304. The operator illustratively sets a height setting for header 1302 (and possibly a tilt or roll angle setting) and a control system controls actuator 1307 (and possibly a tilt or roll actuator—not shown) to maintain header 1302 at the set height above ground 1311 (and at the desired roll angle). The control system responds to header error (e.g., the difference between the set height and measured height of header 1304 above ground 1311 and possibly roll angle error) with a responsiveness that is determined based on a set sensitivity level. If the sensitivity level is set high, the control system responds to, smaller header position errors, and attempts to reduce them more quickly than if the sensitivity is set lower.

After the crop is cut by cutter 1304, it is moved through a conveyor in feeder house 1306 toward feed accelerator 1308, which accelerates the crop into thresher 1310. The crop is threshed by rotor 1312 rotating the crop against concaves 1314. The threshed crop is moved by a separator rotor in separator 1316 where some of the residue is moved by discharge beater 1326 toward the residue subsystem 1338. It can be chopped by residue chopper 1340 and spread on the field by spreader 1342. In other configurations, the residue is simply chopped and dropped in a windrow, instead of being chopped and spread.

Grain falls to cleaning shoe (or cleaning subsystem) 1318. Chaffer 1322 separates some of the larger material from the grain, and sieve 1324 separates some of the finer material from the clean grain. Clean grain falls to an auger in clean grain elevator 1330, which moves the clean grain upward and deposits it in clean grain tank 1332. Residue can be removed from the cleaning shoe 1318 by airflow generated by cleaning fan 1320. Cleaning fan 1320 directs air along an airflow path upwardly through the sieves and chaffers and the airflow carries residue can also be rearwardly in combine 1300 toward the residue handling subsystem 1338.

Tailings can be moved by tailings elevator 1328 back to thresher 1310 where they can be re-threshed. Alternatively, the tailings can also be passed to a separate re-threshing mechanism (also using a tailings elevator or another transport mechanism) where they can be re-threshed as well.

FIG. 14 also shows that, in one example, combine 1300 can include ground speed sensor 1346, one or more separator loss sensors 1348, a clean grain camera 1350, and one or more cleaning shoe loss sensors 1352. Ground speed sensor 1346 illustratively senses the travel speed of combine 1300 over the ground. This can be done by sensing the speed of rotation of the wheels 1344, the drive shaft, the axel, or other components. The travel speed can also be sensed by a positioning system (or position sensor) 918, such as a global positioning system (GPS), a dead reckoning system, a LORAN system, or a wide variety of other systems or sensors that provide an indication of travel speed.

Cleaning shoe loss sensors 1352 illustratively provide an output signal indicative of the quantity of grain loss by both the right and left sides of the cleaning shoe 1318. In one example, sensors 1352 are impact sensors which count grain strikes per unit of time (or per unit of distance traveled) to provide an indication of the cleaning shoe grain loss. The impact sensors for the right and left sides of the cleaning shoe can provide individual signals, or a combined or aggregated signal. It will be noted that sensors 1352 can comprise only a single sensor as well, instead of separate sensors for each shoe.

Separator loss sensor 1348 provides a signal indicative of grain loss in the left and right separators. The sensors associated with the left and right separators can provide separate grain loss signals or a combined or aggregate signal. This can be done using a wide variety of different types of sensors as well. It will be noted that separator loss sensors 1348 may also comprise only a single sensor, instead of separate left and right sensors.

It will also be appreciated that sensor(s) and measurement mechanisms (in addition to the sensors already described) can include other sensors on combine 1300 as well. For instance, the sensors can include tank level sensors 914 that sense the fill level of harvested material in clean grain tank 1332. A header height sensor can sense a height of header 1302 above ground 1311. Sensors can include stability sensors that sense oscillation or bouncing motion (and amplitude) of combine 1300. Sensors can include a residue setting sensor that is configured to sense whether machine 1300 is configured to chop the residue, drop a windrow, etc. The sensors can include cleaning shoe fan speed sensors that can be configured proximate fan 1320 to sense the speed of the fan. The sensors can include a threshing clearance sensor that senses clearance between the rotor 1312 and concaves 1314. The sensors include a threshing rotor speed sensor that senses a rotor speed of rotor 1312. The sensors can include a chaffer clearance sensor that senses the size of openings in chaffer 1322. The sensors can include a sieve clearance sensor that senses the size of openings in sieve 1324. The sensors can include a material other than grain (MOG) moisture sensor that can be configured to sense the moisture level of the material other than grain that is passing through combine 1300. The sensors can include machine setting sensors that are configured to sense the various configurable settings on combine 1300. The sensors can also include a machine orientation sensor that can be any of a wide variety of different types of sensors that sense the orientation of combine 1300. Crop property sensors can sense the type of crop and a variety of different types of crop properties, such as crop type, crop size (e.g., stalk width), crop moisture, and other crop properties. The crop property sensors can also be configured to sense characteristics of the crop as they are being processed by combine 1100. For instance, the crop property sensors can sense grain feed rate (e.g., mass flow rate), as it travels through clean grain elevator 1330, or provide other output signals indicative of other sensed variables. Environment sensors can sense soil moisture, soil compaction, weather (which may be sensed or downloaded), temperature, standing water, and other properties of the soil, crop, machine or environment. Some additional examples of the types of sensors that can be used are described below.

Figure 15:
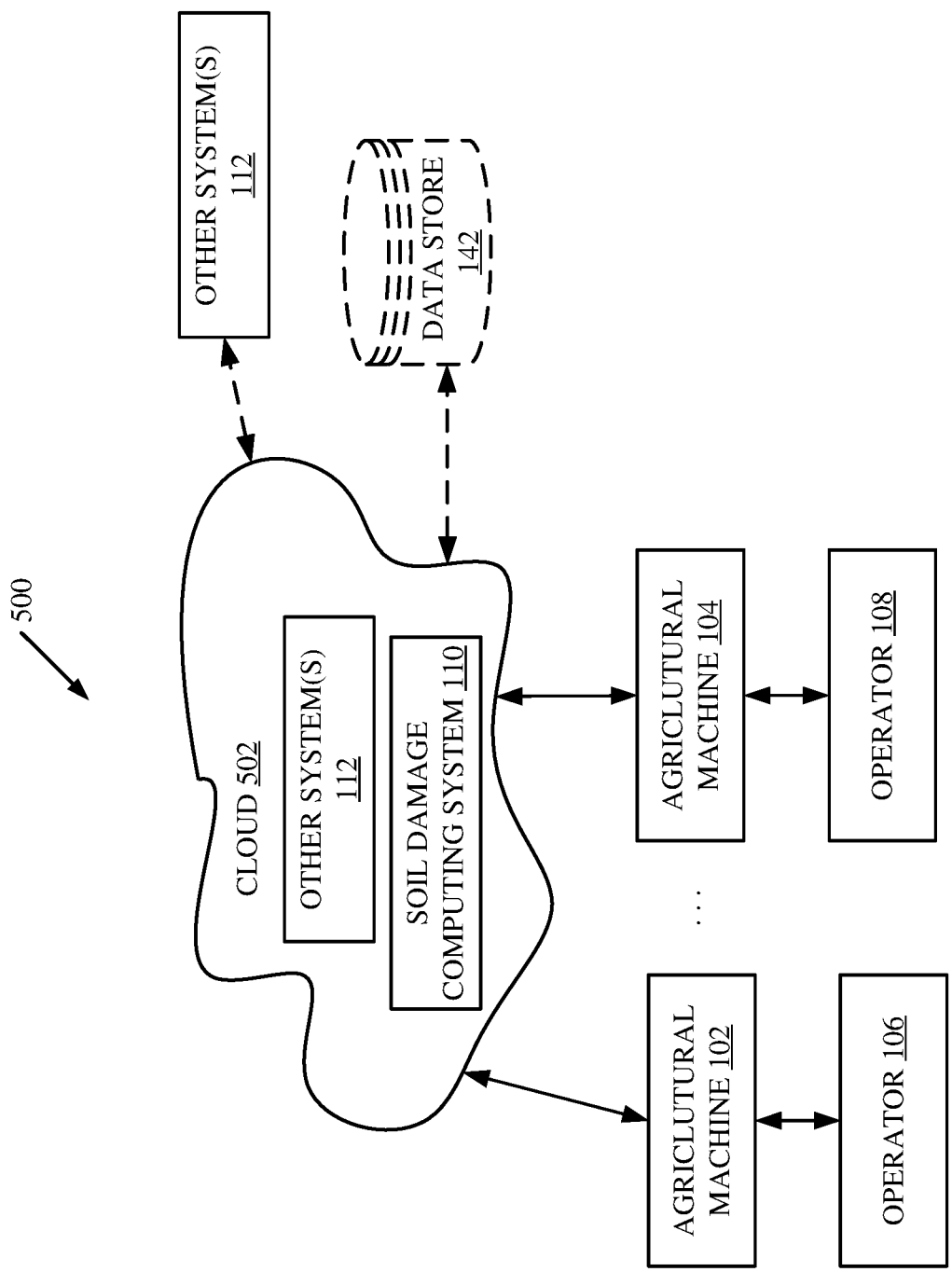
FIG. 15 is a block diagram showing one example of the agricultural system shown in FIG. 7, deployed in a remote server environment.

FIG. 15 is a block diagram of agricultural machines 102-104, shown in FIG. 1, except that it communicates with elements in a remote server architecture 500. In an example, remote server architecture 500 can provide computation, software, data access, and storage services that do not require end-user knowledge of the physical location or configuration of the system that delivers the services. In various examples, remote servers can deliver the services over a wide area network, such as the internet, using appropriate protocols. For instance, remote servers can deliver applications over a wide area network and they can be accessed through a web browser or any other computing component. Software or components shown in previous FIGS. as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, the components and functions can be provided from a conventional server, or the components and functions can be installed on client devices directly, or in other ways.

In the example shown in FIG. 15, some items are similar to those shown in previous FIGS. and they are similarly numbered. FIG. 15 specifically shows that soil damage computing system and data store 142 can be located at a remote server location 502. Therefore, machines 102-104 access those systems through remote server location 502.

FIG. 15 also depicts another example of a remote server architecture. FIG. 15 shows that it is also contemplated that some elements of previous FIGS are disposed at remote server location 502 while others are not. By way of example, data store 142 or other systems 112 can be disposed at a location separate from location 502, and accessed through the remote server at location 502. Regardless of where the items are located, they can be accessed directly by harvester 100, through a network (either a wide area network or a local area network), the items can be hosted at a remote site by a service, or the items can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an example, where cell coverage is poor or nonexistent, another mobile machine (such as a fuel truck) can have an automated information collection system. As the machines 102-104 come close to the fuel truck for fueling, the system automatically collects the information from the machines 102-104 using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on the machines 102-104 until the machines 102-104 enter a covered location. The machines 102-104, themselves, can then send the information to the main network.

Figure 16:
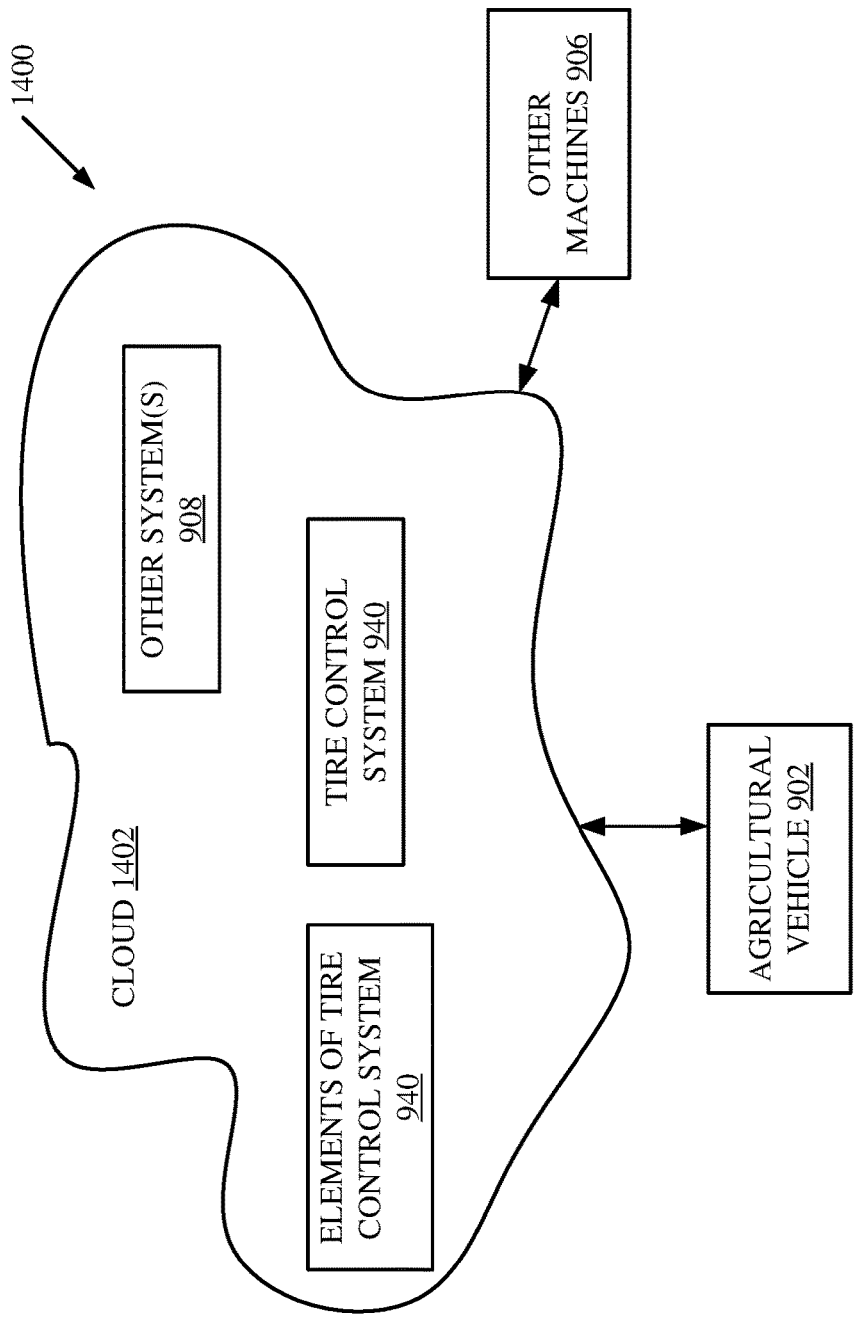
FIG. 16 is a block diagram of one example of the agricultural system deployed in a remote server architecture.

It will also be noted that the elements of previous FIGS., or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, FIG. 16 is a block diagram of agricultural system 900, shown in FIG. 7, except that it communicates with elements in a remote server architecture 1400. In an example, remote server architecture 1400 can provide computation, software, data access, and storage services that do not require end-user knowledge of the physical location or configuration of the system that delivers the services. In various examples, remote servers can deliver the services over a wide area network, such as the internet, using appropriate protocols. For instance, remote servers can deliver applications over a wide area network and they can be accessed through a web browser or any other computing component. Software or components shown in previous FIGS. as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, they can be provided from a conventional server, or they can be installed on client devices directly, or in other ways.

In the example shown in FIG. 16, some items are similar to those shown in previous FIGS. and they are similarly numbered. FIG. 16 specifically shows that map tire control system 940 can be located at a remote server location 1402. Therefore, harvester 902 accesses those systems through remote server location 1402.

FIG. 16 also depicts another example of a remote server architecture. FIG. 9 shows that it is also contemplated that some elements of previous FIGS are disposed at remote server location 1402 while others are not. By way of example, those elements can be disposed at a location separate from location 1402, and accessed through the remote server at location 1402. Regardless of where they are located, they can be accessed directly by vehicle 902, through a network (either a wide area network or a local area network), they can be hosted at a remote site by a service, or they can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an example, where cell coverage is poor or nonexistent, another mobile machine (such as a fuel truck) can have an automated information collection system. As the vehicle 902 comes close to the fuel truck for fueling, the system automatically collects the information from the vehicle 902 using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on the vehicle 902 until the vehicle 902 enters a covered location. The vehicle 902, itself, can then send the information to the main network.

It will also be noted that the elements of previous FIGS., or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 17:
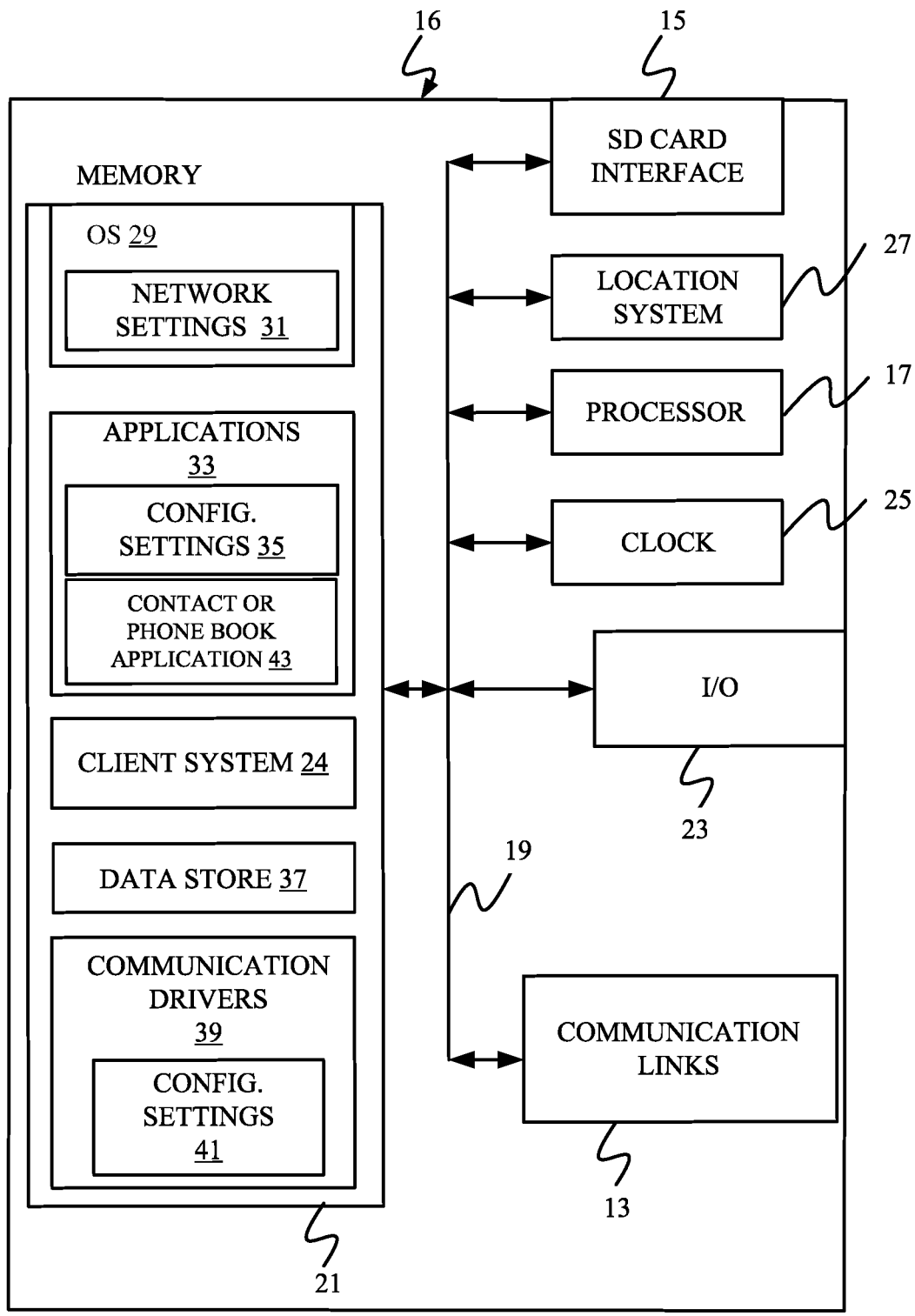
FIGS. 17-19 are block diagrams of mobile devices that can be used in the architectures and systems and machines shown in previous FIGS.
Figure 18:
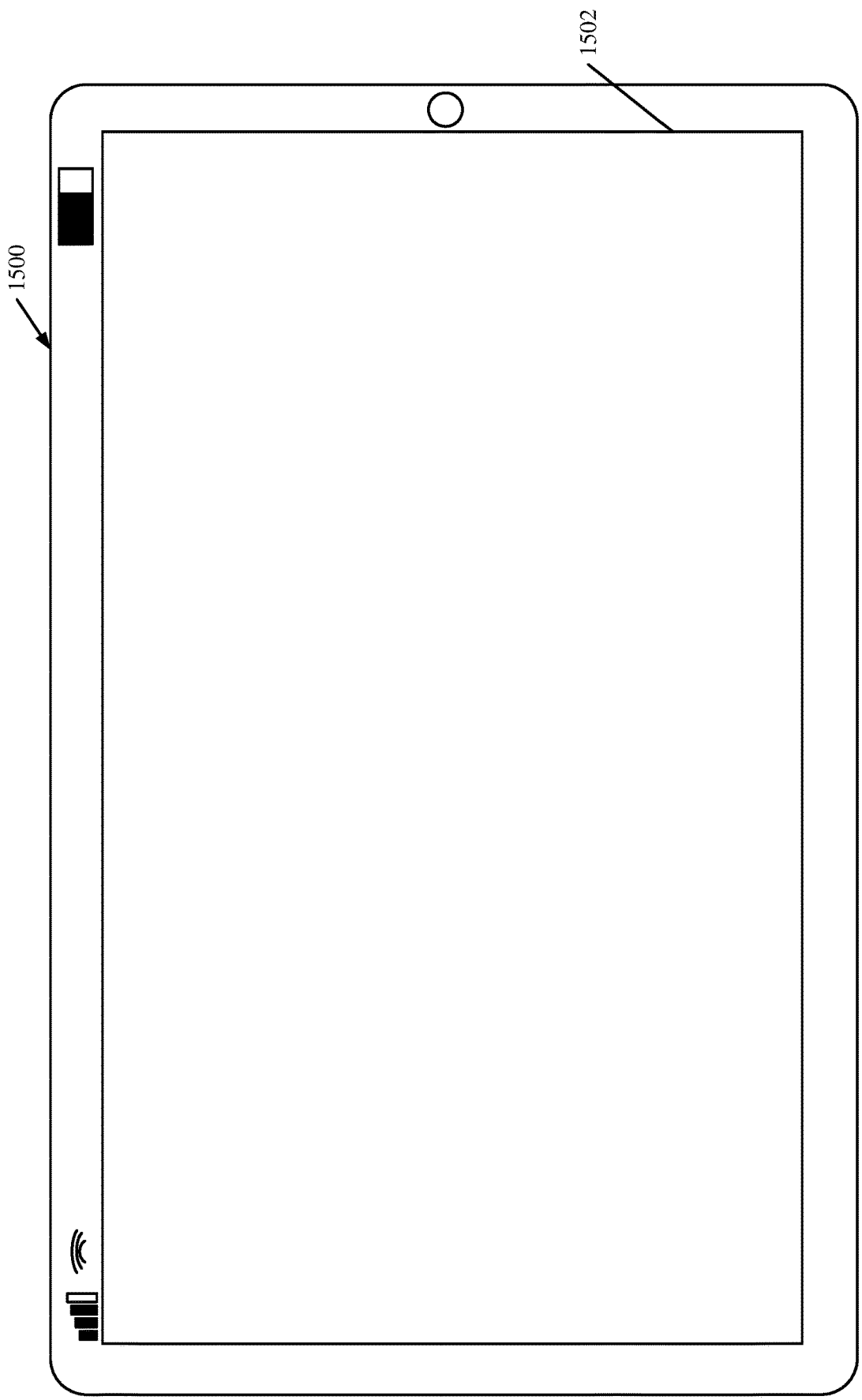
Figure 19:
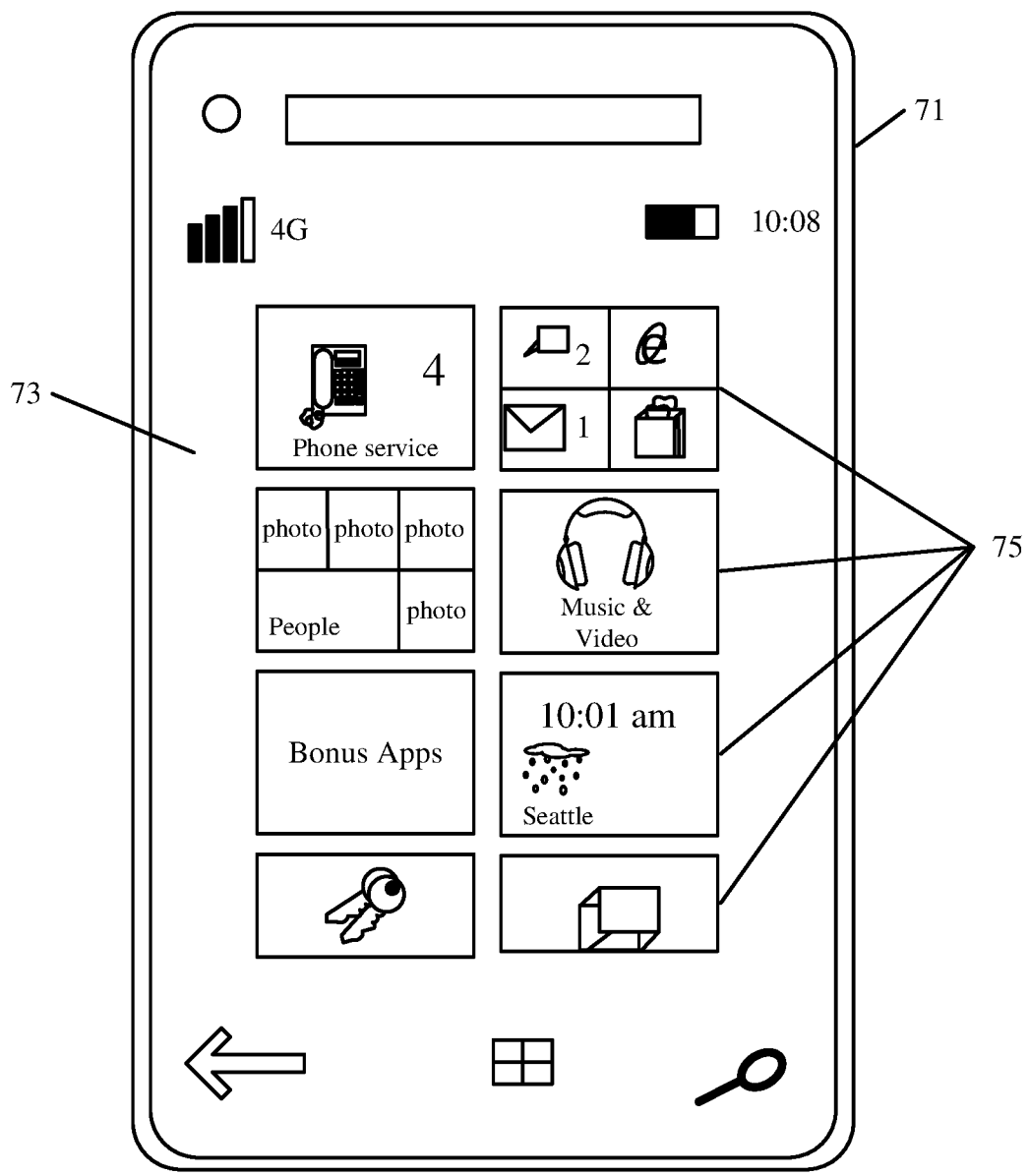

FIG. 17 is a simplified block diagram of one illustrative example of a handheld or mobile computing device that can be used as a user's or client's hand held device 16, in which the present system (or parts of it) can be deployed. For instance, a mobile device can be deployed in the operator compartment of vehicle 902 for use in generating, processing, or displaying tire inflation pressure data or other data. FIGS. 17-19 are examples of handheld or mobile devices.

FIG. 17 provides a general block diagram of the components of a client device 16 that can run some components shown in previous FIGS., that interacts with them, or both. In the device 16, a communications link 13 is provided that allows the handheld device to communicate with other computing devices and under some examples provides a channel for receiving information automatically, such as by scanning. Examples of communications link 13 include allowing communication though one or more communication protocols, such as wireless services used to provide cellular access to a network, as well as protocols that provide local wireless connections to networks.

In other examples, applications can be received on a removable Secure Digital (SD) card that is connected to an interface 15. Interface 15 and communication links 13 communicate with a processor 17 (which can also embody processors or servers from previous FIGS.) along a bus 19 that is also connected to memory 21 and input/output (I/O) components 23, as well as clock 25 and location system 27.

I/O components 23, in one example, are provided to facilitate input and output operations. I/O components 23 for various examples of the device 16 can include input components such as buttons, touch sensors, optical sensors, microphones, touch screens, proximity sensors, accelerometers, orientation sensors and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system (or position system) 27 illustratively includes a component that outputs a current geographical location of device 16. This can include, for instance, a global positioning system (GPS) receiver, a LORAN system, a dead reckoning system, a cellular triangulation system, or other positioning system. System 27 can also include, for example, mapping software or navigation software that generates desired maps, navigation routes and other geographic functions.

Memory 21 stores operating system 29, network settings 31, applications 33, application configuration settings 35, data store 37, communication drivers 39, and communication configuration settings 41. Memory 21 can include all types of tangible volatile and non-volatile computer-readable memory devices. Memory 21 can also include computer storage media (described below). Memory 21 stores computer readable instructions that, when executed by processor 17, cause the processor to perform computer-implemented steps or functions according to the instructions. Processor 17 can be activated by other components to facilitate their functionality as well.

FIG. 18 shows one example in which device 16 is a tablet computer 1500. In FIG. 18, computer 1500 is shown with user interface display screen 1502. Screen 1502 can be a touch screen or a pen-enabled interface that receives inputs from a pen or stylus. Computer 1500 can also use an on-screen virtual keyboard. Computer 1500 might also be attached to a keyboard or other user input device through a suitable attachment mechanism, such as a wireless link or USB port, for instance. Computer 1500 can also illustratively receive voice inputs as well.

FIG. 19 shows that the device can be a smart phone 71. Smart phone 71 has a touch sensitive display 73 that displays icons or tiles or other user input mechanisms 75. Mechanisms 75 can be used by a user to run applications, make calls, perform data transfer operations, etc. In general, smart phone 71 is built on a mobile operating system and offers more advanced computing capability and connectivity than a feature phone.

Note that other forms of the devices 16 are possible.

Figure 20:
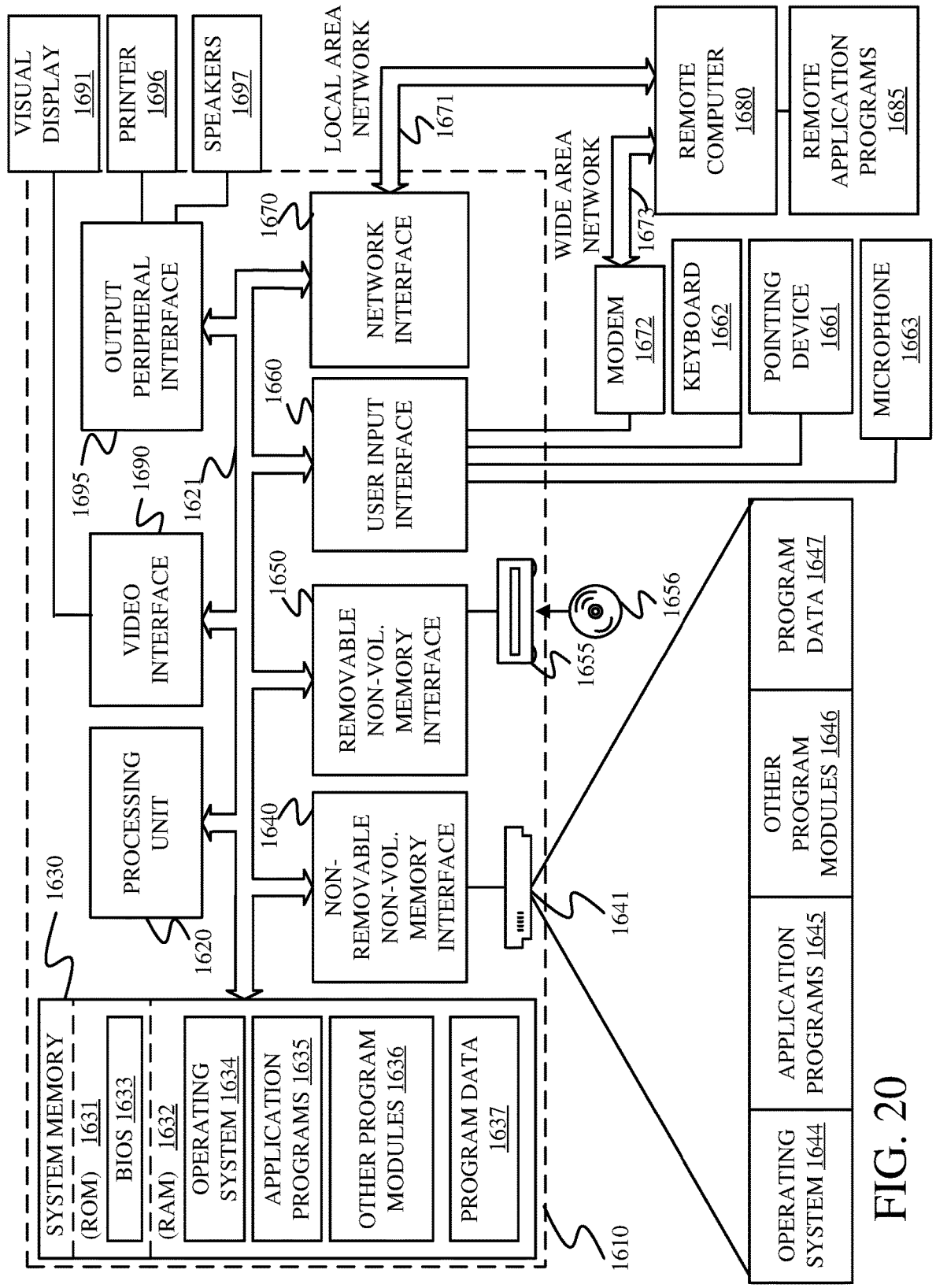
FIG. 20 is a block diagram of one example of a computing environment which can be used in the agricultural system and other systems and machines shown in other FIGS.

FIG. 20 is one example of a computing environment in which elements of previous FIGS., or parts of it, (for example) can be deployed. With reference to FIG. 20, an example system for implementing some embodiments includes a computing device in the form of a computer 1610 programmed to operate as described above. Components of computer 1610 may include, but are not limited to, a processing unit 1620 (which can comprise processors or servers from previous FIGS.), a system memory 1630, and a system bus 1621 that couples various system components including the system memory to the processing unit 1620. The system bus 1621 may be any of several types of bus structures including a memory bus or memory controller, a peripheral bus, and a local bus using any of a variety of bus architectures. Memory and programs described with respect to previous FIGS. can be deployed in corresponding portions of FIG. 10.

Computer 1610 typically includes a variety of computer readable media. Computer readable media can be any available media that can be accessed by computer 1610 and includes both volatile and nonvolatile media, removable and non-removable media. By way of example, and not limitation, computer readable media may comprise computer storage media and communication media. Computer storage media is different from, and does not include, a modulated data signal or carrier wave. Computer storage media includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 1630 includes computer storage media in the form of volatile and/or nonvolatile memory such as read only memory (ROM) 1631 and random access memory (RAM) 1632. A basic input/output system 1633 (BIOS), containing the basic routines that help to transfer information between elements within computer 1610, such as during start-up, is typically stored in ROM 1631. RAM 1632 typically contains data and/or program modules that are immediately accessible to and/or presently being operated on by processing unit 1620. By way of example, and not limitation, FIG. 20 illustrates operating system 1634, application programs 1635, other program modules 1636, and program data 1637.

The computer 1610 may also include other removable/non-removable volatile/nonvolatile computer storage media. By way of example only, FIG. 20 illustrates a hard disk drive 1641 that reads from or writes to non-removable, nonvolatile magnetic media, an optical disk drive 1655, and non-volatile optical disk 1656. The hard disk drive 1641 is typically connected to the system bus 1621 through a non-removable memory interface such as interface 1640, and optical disk drive 1655 are typically connected to the system bus 1621 by a removable memory interface, such as interface 1650.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 20, provide storage of computer readable instructions, data structures, program modules and other data for the computer 1610. In FIG. 20, for example, hard disk drive 1641 is illustrated as storing operating system 1644, application programs 1645, other program modules 1646, and program data 1647. Note that these components can either be the same as or different from operating system 1634, application programs 1635, other program modules 1636, and program data 1637.

A user may enter commands and information into the computer 1610 through input devices such as a keyboard 1662, a microphone 1663, and a pointing device 1661, such as a mouse, trackball or touch pad. Other input devices (not shown) may include a joystick, game pad, satellite dish, scanner, or the like. These and other input devices are often connected to the processing unit 1620 through a user input interface 1660 that is coupled to the system bus, but may be connected by other interface and bus structures. A visual display 1691 or other type of display device is also connected to the system bus 1621 via an interface, such as a video interface 1690. In addition to the monitor, computers may also include other peripheral output devices such as speakers 1697 and printer 1696, which may be connected through an output peripheral interface 1695.

The computer 1610 is operated in a networked environment using logical connections (such as a controller area network—CAN, local area network—LAN, or wide area network WAN) to one or more remote computers, such as a remote computer 1680.

When used in a LAN networking environment, the computer 1610 is connected to the LAN 1671 through a network interface or adapter 1670. When used in a WAN networking environment, the computer 1610 typically includes a modem 1672 or other means for establishing communications over the WAN 1673, such as the Internet. In a networked environment, program modules may be stored in a remote memory storage device. FIG. 20 illustrates, for example, that remote application programs 1685 can reside on remote computer 1680.

It should also be noted that the different examples described herein can be combined in different ways. That is, parts of one or more examples can be combined with parts of one or more other examples. All of this is contemplated herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It can thus be seen that the present description provides a mechanism by which soil damage due to driving a heavy machine over a soft field can be measured, predicted, and surfaced for automated control or operator control. The affect or consequence of the soil damage can also be characterized and output. Different settings or mechanisms can be automatically or manually controlled to mitigate predicted soil damage or to avoid operations that will inflict an undesired amount of soil damage on the soil.

The present discussion has mentioned processors and servers. In one example, the processors and servers include computer processors with associated memory and timing circuitry, not separately shown. They are functional parts of the systems or devices to which they belong and are activated by, and facilitate the functionality of the other components or items in those systems.

Also, a number of user interface displays have been discussed. The user interface displays can take a wide variety of different forms and can have a wide variety of different user actuatable input mechanisms disposed thereon. For instance, the user actuatable input mechanisms can be text boxes, check boxes, icons, links, drop-down menus, search boxes, etc. The mechanisms can also be actuated in a wide variety of different ways. For instance, the mechanisms can be actuated using a point and click device (such as a track ball or mouse). The mechanisms can be actuated using hardware buttons, switches, a joystick or keyboard, thumb switches or thumb pads, etc. The mechanisms can also be actuated using a virtual keyboard or other virtual actuators. In addition, where the screen on which the mechanisms are displayed is a touch sensitive screen, the mechanisms can be actuated using touch gestures. Also, where the device that displays them has speech recognition components, the mechanisms can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

It will be noted that the above discussion has described a variety of different systems, components and/or logic. It will be appreciated that such systems, components and/or logic can be comprised of hardware items (such as processors and associated memory, or other processing components, some of which are described below) that perform the functions associated with those systems, components and/or logic. In addition, the systems, components and/or logic can be comprised of software that is loaded into a memory and is subsequently executed by a processor or server, or other computing component, as described below. The systems, components and/or logic can also be comprised of different combinations of hardware, software, firmware, etc., some examples of which are described below. These are only some examples of different structures that can be used to form the systems, components and/or logic described above. Other structures can be used as well.

What is claimed is:

1. A computer implemented method of controlling an agricultural vehicle, comprising:
   detecting a fill level of material in a material holding compartment on the agricultural vehicle;
   identifying a type of material in the material holding compartment; and
   automatically controlling a tire inflation pressure for tires on the agricultural vehicle based on the detected fill level and the identified type of material in the material holding compartment.

2. The computer implemented method of claim 1 wherein automatically controlling a tire inflation pressure comprises:
   identifying a target inflation pressure for the tires based on the fill level and the identified type of material in the material holding compartment.

3. The computer implemented method of claim 2 wherein automatically controlling a tire inflation pressure comprises:
   controlling a controllable tire inflation subsystem to adjust inflation pressure in the tires to the target inflation pressure.

4. The computer implemented method of claim 3 wherein controlling the controllable tire inflation subsystem comprises:
   detecting a current inflation pressure in the tires; and
   controlling the controllable tire inflation subsystem based on the current inflation pressure and the target inflation pressure.

5. The computer implemented method of claim 2 wherein identifying a target inflation pressure comprises:
   identifying a load on the tires based on the fill level and the identified type of material in the material holding compartment; and
   identifying the target inflation pressure for the tires based on the load on the tires.

6. The computer implemented method of claim 3 wherein identifying a target inflation pressure comprises:
   identifying a separate target inflation pressure corresponding to each of a plurality of different subsets of the tires and wherein automatically controlling the tire inflation pressure comprises controlling the controllable tire inflation subsystem to adjust each of the different subsets of the tires based on the corresponding target inflation pressure.

7. The computer implemented method of claim 5 wherein automatically controlling comprises:
   detecting a tire inflation control trigger; and
   automatically controlling the tire inflation pressure based on detecting the tire inflation control trigger.

8. The computer implemented method of claim 7 wherein detecting a tire inflation control trigger comprises:
   detecting a geographic location of the agricultural vehicle; and
   detecting the tire inflation control trigger based on the detected geographic location.

9. The computer implemented method of claim 8 wherein detecting the geographic location comprises:
   detecting a distance traveled by the agricultural vehicle and wherein detecting the tire inflation control trigger comprises detecting the tire inflation control trigger based on the distance traveled.

10. The computer implemented method of claim 7 wherein detecting a tire inflation control trigger comprises:
    detecting a change in the load on the tires; and
    detecting the tire inflation control trigger based on the change in the load on the tires.

11. The computer implemented method of claim 7 wherein detecting a tire inflation control trigger comprises:
    detecting a change in the fill level of the material in the material holding compartment; and
    detecting the tire inflation control trigger based on the change in the fill level.

12. An agricultural system, comprising:
    an agricultural vehicle having a material holding compartment and a set of tires;
    a level sensor detecting a fill level of material in the material holding compartment on the agricultural vehicle;
    a material identification system configured to identify a type of material in the material holding compartment; and
    a tire control system automatically controlling tire inflation pressure for the tires on the agricultural vehicle based on the detected fill level and the identified type of material in the material holding compartment.

13. The agricultural system of claim 12 and further comprising:
    a controllable tire inflation subsystem configured to adjust inflation pressure in the tires, wherein the tire control system is configured to identify a target inflation pressure for the tires based on the fill level and the identified type of material the material holding compartment and to control the controllable tire inflation subsystem based on the target inflation pressure.

14. The agricultural system of claim 13 wherein the tire control system comprises:

a tire inflation control system configured to detect a current inflation pressure in the tires and control the controllable tire inflation subsystem based on the current inflation pressure and the target inflation pressure.

15. The agricultural system of claim 14 wherein the tire control system comprises:

a load identification system configured to identify a load on the tires based on the fill level and the identified type of material in the material holding compartment, the tire inflation control system being configured to identify the target inflation pressure for the tires based on the load on the tires.

16. The agricultural system of claim 14 wherein the load identification system is configured to identify a separate target inflation pressure corresponding to each of a plurality of different subsets of the tires and automatically control the tire inflation pressure by controlling the controllable tire inflation subsystem to adjust each of the different subsets of the tires based on the corresponding target inflation pressure.

17. A computer system, comprising:

at least one processor; and a data store that stores computer executable instructions which, when executed by the at least one processor, cause the at least one processor to perform steps, comprising:

detecting a vehicle index based on a fill level of material in a material holding compartment on the agricultural vehicle and an identified type of material in the material holding compartment;

identifying a target inflation pressure for the tires based on a load bearing characteristic of soil over which the agricultural vehicle is traveling and based on the vehicle index; and controlling a controllable tire inflation subsystem to adjust inflation pressure in the tires to the target inflation pressure.

18. The computer system of claim 17 wherein identifying a target inflation pressure comprises:

identifying a load on the tires based on the fill level and the identified type of material in the material holding compartment; and identifying the target inflation pressure for the tires based on the load on the tires.

* * * * *